United States Patent
Meskens

(10) Patent No.: US 10,080,893 B2
(45) Date of Patent: Sep. 25, 2018

(54) VARYING THE EFFECTIVE COIL AREA FOR AN INDUCTIVE TRANSCUTANEOUS POWER LINK

(71) Applicant: Cochlear Limited, Macquarie University, NSW (AU)

(72) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 403 days.

(21) Appl. No.: 14/673,133

(22) Filed: Mar. 30, 2015

(65) Prior Publication Data

US 2015/0202438 A1 Jul. 23, 2015

Related U.S. Application Data

(62) Division of application No. 12/834,577, filed on Jul. 12, 2010, now Pat. No. 8,996,121.

(51) Int. Cl.
| | |
|---|---|
| *A61N 1/00* | (2006.01) |
| *A61N 1/36* | (2006.01) |
| *A61N 1/378* | (2006.01) |
| *A61N 1/372* | (2006.01) |

(52) U.S. Cl.
CPC ..... *A61N 1/36032* (2013.01); *A61N 1/36036* (2017.08); *A61N 1/3787* (2013.01); *A61N 1/37229* (2013.01)

(58) Field of Classification Search
CPC .............. A61N 1/36032; A61N 1/3787; A61N 1/37229
See application file for complete search history.

(56) References Cited

U.S. PATENT DOCUMENTS

| | | | |
|---|---|---|---|
| 4,441,210 A | 4/1984 | Hochmair et al. | |
| 4,532,930 A | 8/1985 | Crosby et al. | |
| 4,741,339 A | 5/1988 | Harrison et al. | |
| 5,070,535 A | 12/1991 | Hochmair et al. | |
| 5,314,453 A | 5/1994 | Jeutter | |
| 5,755,748 A | 5/1998 | Borza | |
| 5,991,664 A | 11/1999 | Seligman | |
| 6,088,619 A * | 7/2000 | Hein ................... | A61N 1/3787 607/61 |
| 6,212,431 B1 | 4/2001 | Hahn et al. | |
| 6,246,911 B1 | 6/2001 | Seligman | |
| 6,321,118 B1 | 11/2001 | Hahn | |

(Continued)

*Primary Examiner* — Mallika D Fairchild
(74) *Attorney, Agent, or Firm* — Piloff & Passino LLP; Martin J. Cosenza

(57) ABSTRACT

A prosthesis including an external device and an implantable component. The external device includes a first inductive communication component. The implantable component includes a second inductive communication component, wherein the implantable component is configured to be implanted under skin of a recipient. The external device is configured to transmit power via magnetic induction transcutaneoulsy to the implantable component via the second inductive communication component. The internal component is configured to receive at least a portion of the power transmitted from the external device via the inductive communication component. At least one of the first and second inductive communication components comprise an inductive communication component configured to vary its effective coil area.

13 Claims, 22 Drawing Sheets

(56) References Cited

U.S. PATENT DOCUMENTS

| | | |
|---|---|---|
| 6,473,652 B1 | 10/2002 | Sarwal et al. |
| 7,186,209 B2 | 3/2007 | Jacobson et al. |
| 7,209,792 B1 | 4/2007 | Parramon et al. |
| 7,286,880 B2 | 10/2007 | Olson et al. |
| 7,286,881 B2 | 10/2007 | Schommer et al. |
| 2007/0055321 A1 | 3/2007 | Gordon et al. |
| 2007/0118185 A1 | 5/2007 | Shaquer |
| 2008/0172109 A1 | 7/2008 | Rahman et al. |
| 2011/0009924 A1 | 1/2011 | Meskens |
| 2011/0101790 A1* | 5/2011 | Budgett ................ A61M 1/127 307/104 |

* cited by examiner

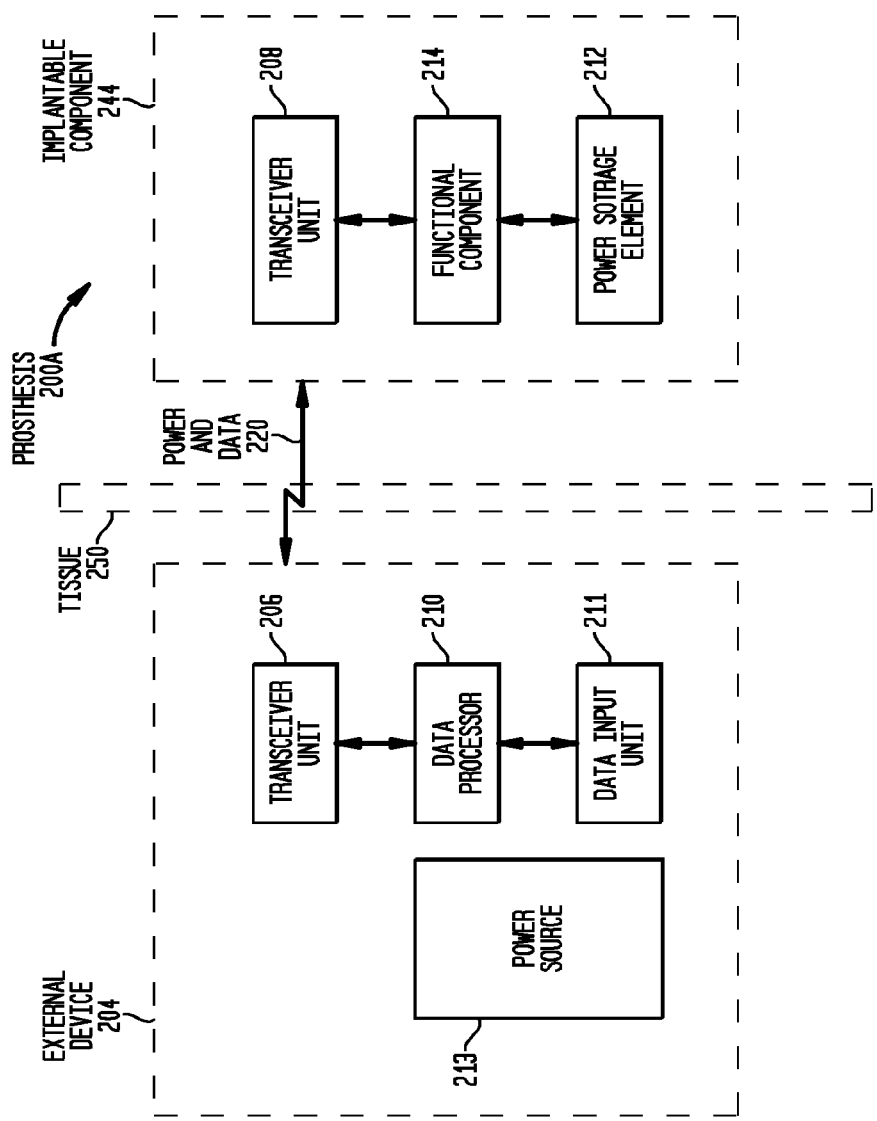

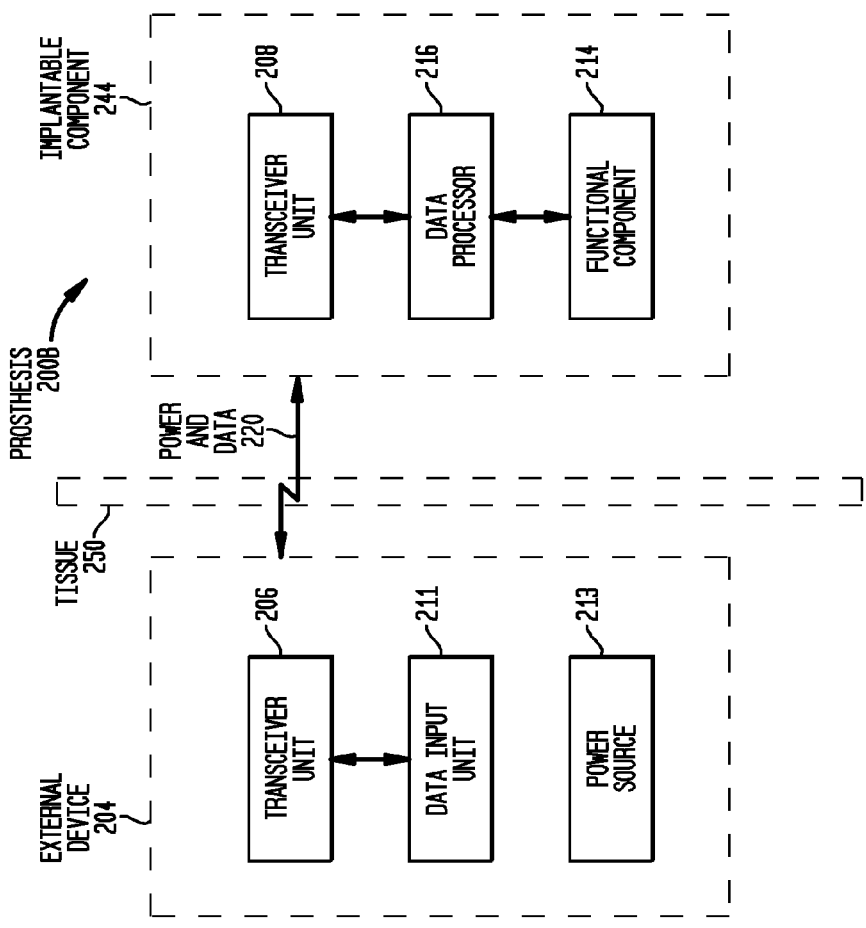

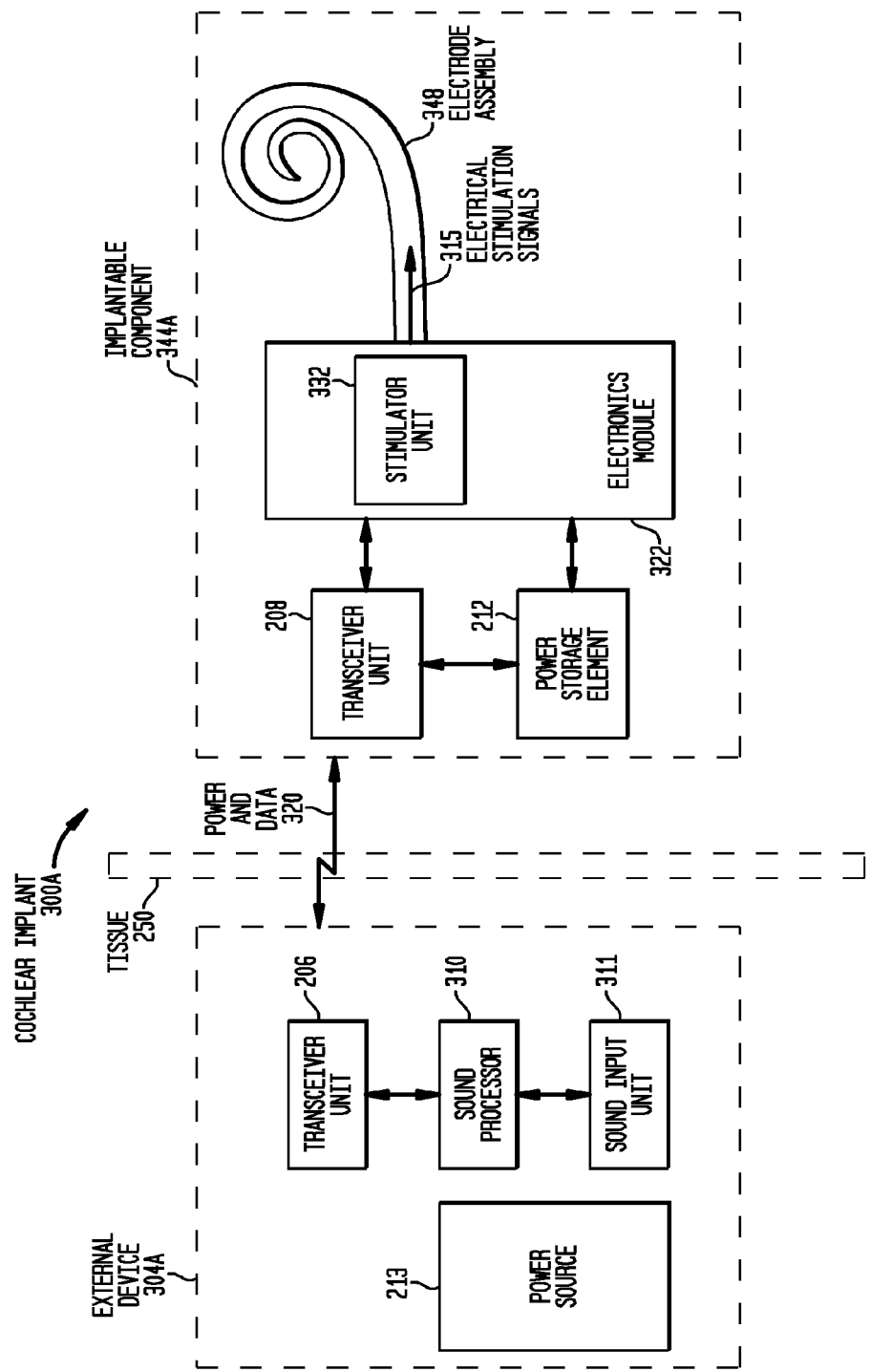

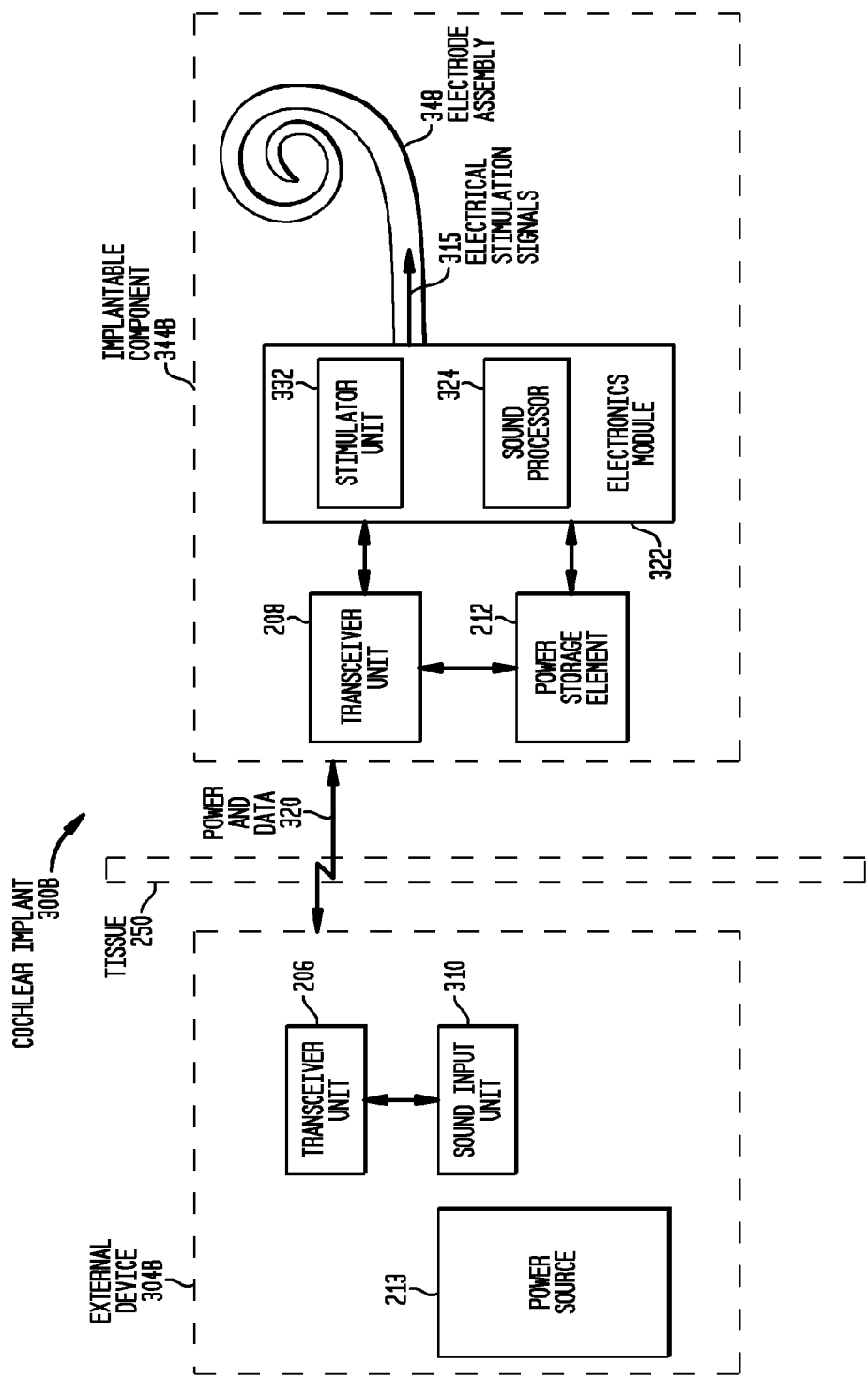

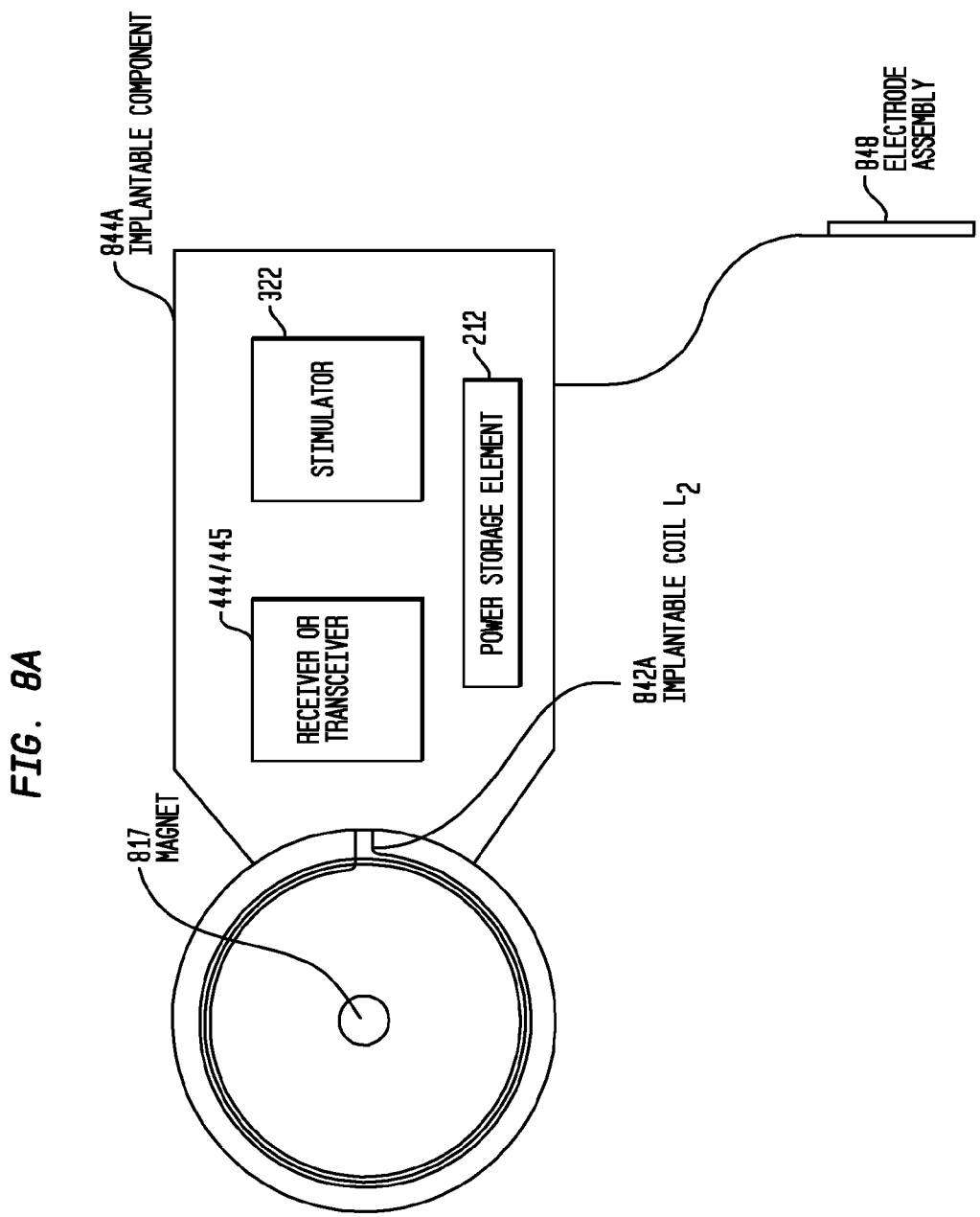

VARYING THE EFFECTIVE COIL AREA FOR AN INDUCTIVE TRANSCUTANEOUS POWER LINK

CROSS-REFERENCE TO RELATED APPLICATIONS

The present application is a Divisional application of U.S. patent application Ser. No. 12/834,577, filed Jul. 12, 2010, naming Werner Meskens as an inventor, the entire contents of that application being incorporated herein by reference in its entirety.

The present application claims priority from Australian Provisional Patent Application No. 2009-903236 entitled "Inductive Power Link Optimisation," filed Jul. 10, 2009, which is hereby incorporated by reference herein.

BACKGROUND

Field of the Invention

The present invention relates generally to methods, devices and systems for transcutaneous inductive power links, and more specifically, to varying the effective coil area for an inductive transcutaneous power link.

Related Art

Medical devices having one or more implantable components, generally referred to as implantable medical devices, have provided a wide range of therapeutic benefits to patients over recent decades. In particular, devices such as hearing aids, implantable pacemakers, defibrillators, functional electrical stimulation devices, such as cochlear prostheses, organ assist or replacement devices, and other partially or completely-implanted medical devices, have been successful in performing life saving and/or lifestyle enhancement functions for a number of years.

The type and function of implantable medical devices has increased over the years. For example, many such implantable medical devices often include one or more instruments, apparatus, sensors, processors, controllers or other functional mechanical, electrical or electronic components that are permanently or temporarily implanted in a patient. Such medical devices may be used to perform diagnosis, prevention, monitoring, treatment or management of a disease or injury or symptom thereof, or to investigate, replace or modify of the anatomy or of a physiological process. Many implantable components receive power and/or data from external components that are part of, or operate in conjunction with, the implantable component. For example, some implantable medical devices include a power source integrated into the implantable component.

A cochlear prosthesis is a specific type of hearing prostheses that delivers electrical stimulation to the recipient's cochlea. As used herein, cochlear implants also include hearing prostheses that deliver electrical stimulation in combination with other types of stimulation, such as acoustic or mechanical stimulation.

Implantable medical devices, including cochlear implants, sometimes rely on an inductive link in order to transfer power to an implanted power consuming device. In an active implantable system such as a cochlear implant having an external coil and an implanted coil, the power transfer between the coils is based on magnetic induction between the coils.

SUMMARY

According to a first aspect of the present invention, there is provided a prosthesis comprising an external device and an implantable component. The external device includes a first inductive communication component. The implantable component includes a second inductive communication component, wherein the implantable component is configured to be implanted under skin of a recipient. The external device is configured to transmit power via magnetic induction transcutaneoulsy to the implantable component via the first inductive communication component. The internal component is configured to receive at least a portion of the power transmitted from the external device via the second inductive communication component. At least one of the first and second inductive communication components comprises an inductive communication component configured to vary its effective coil area.

According to another aspect of the present invention, there is a method transcutaneously transmitting power from an external device to an implantable component of a prosthesis implanted in a recipient. The method comprises transmitting power during a first temporal period from the external device through skin of the recipient to the implantable component via an inductive communication component system. The method further comprises varying, after the first temporal period, the coupling factor k of the inductive communication component system and transmitting, after the first temporal period and after varying the coupling factor k, power from the external device through skin of the recipient to the implantable component of the prosthesis via the inductive communication component system.

According to yet another aspect of the present invention, there is a system for transcutaneously transmitting power from an external device to an implantable component of a prosthesis implanted in a recipient. The system comprises an external device including an external inductive communication component and an implantable component including an implanted inductive communication component. The effective coil area of the external inductive communication component is substantially different from the effective coil area of the implanted inductive communication component.

BRIEF DESCRIPTION OF THE DRAWINGS

Embodiments of the present invention are described below with reference to the attached drawings, in which:

FIG. 2A is a functional block diagram of a prosthesis, in accordance with embodiments of the present invention;

FIG. 2B is an alternate functional block diagram of a prosthesis, in accordance with embodiments of the present invention;

FIG. 3A is a functional block diagram of a cochlear implant, in accordance with embodiments of the present invention;

FIG. 3B is an alternate functional block diagram of a cochlear implant, in accordance with embodiments of the present invention;

FIG. 8A is a simplified schematic diagram of an implantable component including a standard coil in accordance with embodiments of the present invention;

DETAILED DESCRIPTION

Aspects of the present invention are generally directed to a transcutaneous power and/or data link in a prosthesis, such as an implantable medical device, over which power and/or data are transmitted to a receiver unit within an implantable component.

A prosthesis in accordance with an embodiment of the present invention comprises an external device and an implantable component. The external device includes a first inductive communication component. The implantable component includes a second inductive communication component, wherein the implantable component is configured to be implanted under skin of a recipient. The external device is configured to transmit power via magnetic induction transcutaneously to the implantable component via the first inductive communication component. The internal component is configured to receive at least a portion of the power transmitted from the external device via the second inductive communication component. At least one of the first and second inductive communication components comprises an inductive communication component configured to vary its effective coil area.

Embodiments of the present invention are described herein primarily in connection with one type of implantable medical device, a hearing prosthesis, namely a cochlear prosthesis (commonly referred to as cochlear prosthetic devices, cochlear implants, cochlear devices, and the like; simply "cochlea implants" herein.) Cochlear implants deliver electrical stimulation to the cochlea of a recipient. It should, however, be understood that the current techniques described herein are also applicable to other types of active implantable medical devices (AIMDs), such as, auditory brain stimulators, also sometimes referred to as an auditory brainstem implant (ABI), other implanted hearing aids or hearing prostheses, neural stimulators, retinal prostheses, cardiac related devices such as pacers (also referred to as pacemakers) or defibrillators, implanted drug pumps, electro-mechanical stimulation devices (e.g., direct acoustic cochlear stimulators (DACS)) or other implanted electrical devices.

As used herein, cochlear implants also include hearing prostheses that deliver electrical stimulation in combination with other types of stimulation, such as acoustic or mechanical stimulation (sometimes referred to as mixed-mode devices). It would be appreciated that embodiments of the present invention may be implemented in any cochlear implant or other hearing prosthesis now known or later developed, including auditory brain stimulators, or implantable hearing prostheses that mechanically stimulate components of the recipient's middle or inner ear. For example, embodiments of the present invention may be implemented, for example, in a hearing prosthesis that provides mechanical stimulation to the middle ear and/or inner ear of a recipient.

Figure 1:
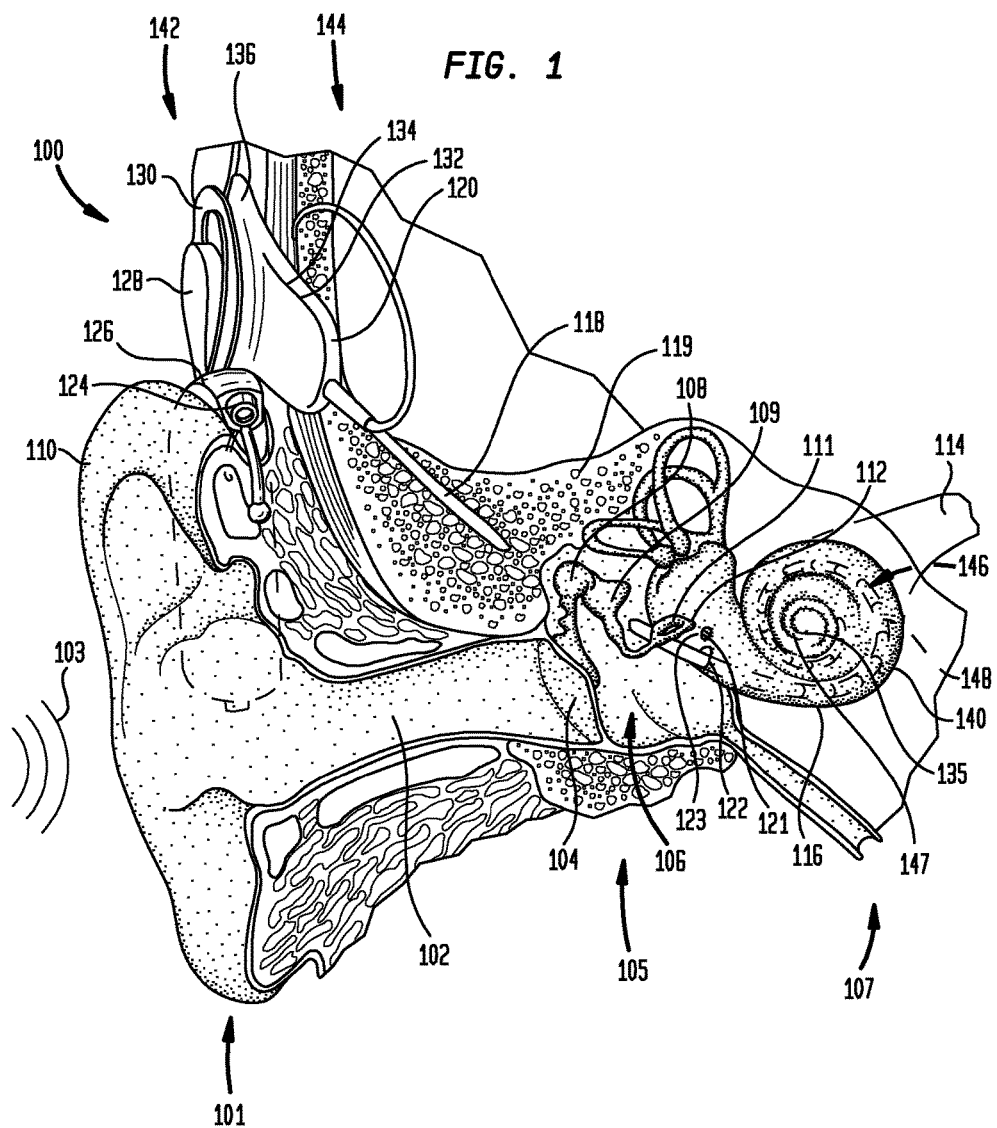
FIG. 1 is a perspective view of a cochlear implant, in which embodiments of the present invention may be implemented.

FIG. 1 is perspective view of a cochlear implant, referred to as cochlear implant system 100 implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant system 100 comprises an external component 142 which is directly or indirectly attached to the body of the recipient, and an internal component 144 which is temporarily or permanently implanted in the recipient. External component 142 is often referred as a sound processor device that typically comprises one or more sound input elements, such as microphone 124 for detecting sound, a processor 126, a power source (not shown), and an external coil driver unit 128 (referred to herein as primary coil interface 128). External coil interface unit 128 is connected to an external coil 130 (also referred to herein as primary coil 130) and, preferably containing a magnet (not shown) secured directly or indirectly concentric to internal coil 136 (also referred to herein as secondary coil 136). External and internal coils are closely coupled enabling power and data transfers by inductive link. Processor 126 processes the output of microphone 124 that is positioned, in the depicted embodiment, behind the ear of the recipient. Processor 126 generates encoded signals, sometimes referred to herein as encoded data signals, which are provided to the external coil interface unit 128 via a cable (not shown).

The internal implant component 144 comprises an internal coil 136 (also referred to herein as secondary coil 136), an implant unit 134, and a stimulating lead assembly 118. As illustrated, implant unit 144 comprises a stimulator unit 120 and a secondary coil interface 132 (also referred to as secondary coil interface 132). Secondary coil interface 132 is connected to the secondary coil 136. Secondary coil 136 may include a magnet (also not shown) fixed in the middle of secondary coil 136. The secondary coil interface 132 and stimulator unit 120 are hermetically sealed within a biocompatible housing, sometimes collectively referred to as a stimulator/receiver unit. The internal coil receives power and stimulation data from primary coil 130. Stimulating lead assembly 118 has a proximal end connected to stimulator unit 120, and a distal end implanted in cochlea 140. Stimulating lead assembly 118 extends from stimulator unit 120 to cochlea 140 through mastoid bone 119. In some embodiments stimulating lead assembly 118 may be implanted at least in basal region 116, and sometimes further. For example, stimulating lead assembly 118 may extend towards apical end of cochlea 140, referred to as cochlea apex 147. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 135 of cochlea 140.

Stimulating lead assembly 118 comprises a longitudinally aligned and distally extending array 146 of electrode contacts 148, sometimes referred to as array of electrode contacts 146 herein. Although array of electrode contacts 146 may be disposed on Stimulating lead assembly 118, in most practical applications, array of electrode contacts 146 is integrated into Stimulating lead assembly 118. As such, array of electrode contacts 146 is referred to herein as being disposed in Stimulating lead assembly 118. Stimulator unit 120 generates stimulation signals which are applied by electrode contacts 148 to cochlea 140, thereby stimulating auditory nerve 114. Because, in cochlear implant 100, Stimulating lead assembly 118 provides stimulation, Stimulating lead assembly 118 is sometimes referred to as a stimulating lead assembly.

In cochlear implant system 100, primary coil 130 transfers electrical signals (that is, power and stimulation data) to the internal or secondary coil 136 via an inductive coupled radio frequency (RF) link. Secondary coil 136 is typically made of multiple turns of electrically insulated single-strand or multi-strand platinum or gold wire. The electrical insulation of secondary coil 136 is provided by a biocompatible wire insulator and a flexible silicone molding (not shown). In use, secondary coil 136 may be positioned in a recess of the temporal bone adjacent auricle 110 of the recipient.

It is noted that embodiments of the present invention may be practiced with implants other than cochlear implants, such as, for example, implanted heart monitors, implanted muscle stimulation devices, etc. Accordingly, an embodiment of the present invention will first be described in the context of a non-descript implant, and later, embodiments of the present invention will be described in the context of a cochlear implant.

FIG. 2A is a functional block diagram of a prosthesis 200A in accordance with embodiments of the present invention. Prosthesis 200A comprises an implantable component 244 configured to be implanted beneath a recipient's skin or other tissue 250 and an external device 204. For example, implantable component 244 may be implantable component 144 of FIG. 1. Similar to the embodiments described above with reference to FIG. 1, implantable component 244 comprises a transceiver unit 208 which receives data and power from external device 204. External device 204 transmits power and data 220 via transceiver unit 206 to transceiver unit 208 via a magnetic induction data link 220. As used herein, the term receiver refers to any device or component configured to receiver power and/or data such as the receiving portion of a transceiver or a separate component for receiving. The details of transmission of power and data to transceiver unit 208 are provided below. With regard to transceivers, it is noted at this time that while embodiments of the present invention may utilize transceivers, separate receivers and/or transmitters may be utilized as appropriate. This will be apparent in view of the description below.

Implantable component 244 may comprises a power storage element 212 and a functional component 214. Power storage element 212 is configured to store power received by transceiver unit 208, and to distribute power, as needed, to the elements of implantable component 244. Power storage element 212 may comprise, for example, a rechargeable battery 212. An example of a functional component may be a stimulator unit 120 as shown in FIG. 1.

In certain embodiments, implantable component 244 may comprise a single unit having all components of the implantable component 244 disposed in a common housing. In other embodiments, implantable component 244 comprises a combination of several separate units communicating via wire or wireless connections. For example, power storage element 212 may be a separate unit enclosed in a hermetically sealed housing.

In the embodiment depicted in FIG. 2A, external device 204 includes a data processor 210 that receives data from data input unit 211 and processes the received data. The processed data from data processor 210 is transmitted by transceiver unit 206 to transceiver unit 208. In an exemplary embodiment, data processor 210 may be a sound processor, such as sound processor 126 in FIG. 1, for a cochlear implant, and data input unit 211 may be a microphone for a cochlear implant (e.g., microphone 124 of FIG. 1).

FIG. 2B presents an alternate embodiment of the prosthesis 200A of FIG. 2A, identified in FIG. 2B as prosthesis 200B. As may be seen from comparing FIG. 2A to FIG. 2B, the data processor may be located in the external device 204 or may be located in the implantable component 244. In some embodiments, both the external device 204 and the implantable component 244 may include a data processor.

As shown in FIGS. 2A and 2B, external device 204 may include a power source 213. Power from power source 213 may be transmitted by transceiver unit 206 to transceiver unit 208 to provide power to the implantable component 244, as will be described in more detail below.

While not shown in FIGS. 2A and 2B, external device 204 and/or implantable component 244 include respective inductive communication components configured to vary their effective coil area, as will be described in more detail below, and thus vary the coupling factor k of the inductive communication component system formed by the inductive communication components. These inductive communication components may be connected to transceiver unit 206 and transceiver unit 208, permitting power and data 220 to be transferred between the two units via magnetic induction.

As used herein, an inductive communication component includes both standard induction coils and inductive communication components configured to vary their effective coil areas.

As noted above, prosthesis 200A of FIG. 2A may be a cochlear implant. In this regard, FIG. 3A provides additional details of an embodiment of FIG. 2A where prosthesis 200A is a cochlear implant. Specifically, FIG. 3A is a functional block diagram of a cochlear implant 300 in accordance with embodiments of the present invention.

It is noted that the components detailed in FIGS. 2A and 2B may be identical to the components detailed in FIG. 3A, and the components of 3A may be used in the embodiments depicted in FIGS. 2A and 2B, as will become apparent below.

Cochlear implant 300A comprises an implantable component 344A (e.g., implantable component 144 of FIG. 1) configured to be implanted beneath a recipient's skin or other tissue 250, and an external device 304A. External device 304A may be an external component such as external component 142 of FIG. 1.

Similar to the embodiments described above with reference to FIGS. 2A and 2B, implantable component 344A comprises a transceiver unit 208 (which may be the same transceiver unit used in FIGS. 2A and 2B) which receives data and power from external device 304A. External device 304A transmits power and data 320 to transceiver unit 208 via a magnetic induction data link, while charging module 202. The details of transmission of power and data to receiver unit 208 are provided below.

Implantable component 344A also comprises a power storage element 212, electronics module 322 (which may include components such as sound processor 126 and/or may include a stimulator unit 322 corresponding to stimulator unit 120 of FIG. 1) and an electrode assembly 348 (which may include an array of electrode contacts 148 of FIG. 1). Power storage element 212 is configured to store power received by transceiver unit 208, and to distribute power, as needed, to the elements of implantable component 344A.

As shown, electronics module 322 includes a stimulator unit 332. Electronics module 322 may also include one or more other functional components used to generate or control delivery of electrical stimulation signals 315 to the recipient. As described above with respect to FIG. 1, electrode assembly 348 is inserted into the recipient's cochlea and is configured to deliver electrical stimulation signals 315 generated by stimulator unit 332 to the cochlea.

In the embodiment depicted in FIG. 3A, the external device 304A includes a sound processor 310 configured to convert sound signals received from sound input unit 311 (e.g., a microphone, an electrical input for an FM hearing system, etc.) into data signals. In an exemplary embodiment, the sound processor 310 corresponds to data processor 210 of FIG. 2A.

FIG. 3B presents an alternate embodiment of a cochlear implant 300B. The elements of cochlear implant 300B correspond to the elements of cochlear implant 300A except that external device 304B does not include sound processor 310. Instead, the implantable component 344B includes a sound processor 324, which may correspond to sound processor 310 of FIG. 3A.

As will be described in more detail below, while not shown in the figures, external device 304A/304B and/or implantable component 344A/344B include respective inductive communication components configured to vary their effective coil area, and thus the coupling factor k of an inductive communication component system formed by the inductive communication components, as will be described in more detail below.

FIGS. 3A and 3B illustrate that external device 304A/304B may include a power source 213, which may be the same as power source 213 depicted in FIG. 2A. Power from power source 213 may be transmitted by transceiver unit 306 to transceiver unit 308 to provide power to the implantable component 344A/344B, as will be detailed below. FIGS. 3A and 3B further detail that the implantable component 344A/344B may include a power storage element 212 that stores power received by the implantable component 344 from power source 213. Power storage element 212 may be the same as power storage element 212 of FIG. 2A.

Figure 3C:
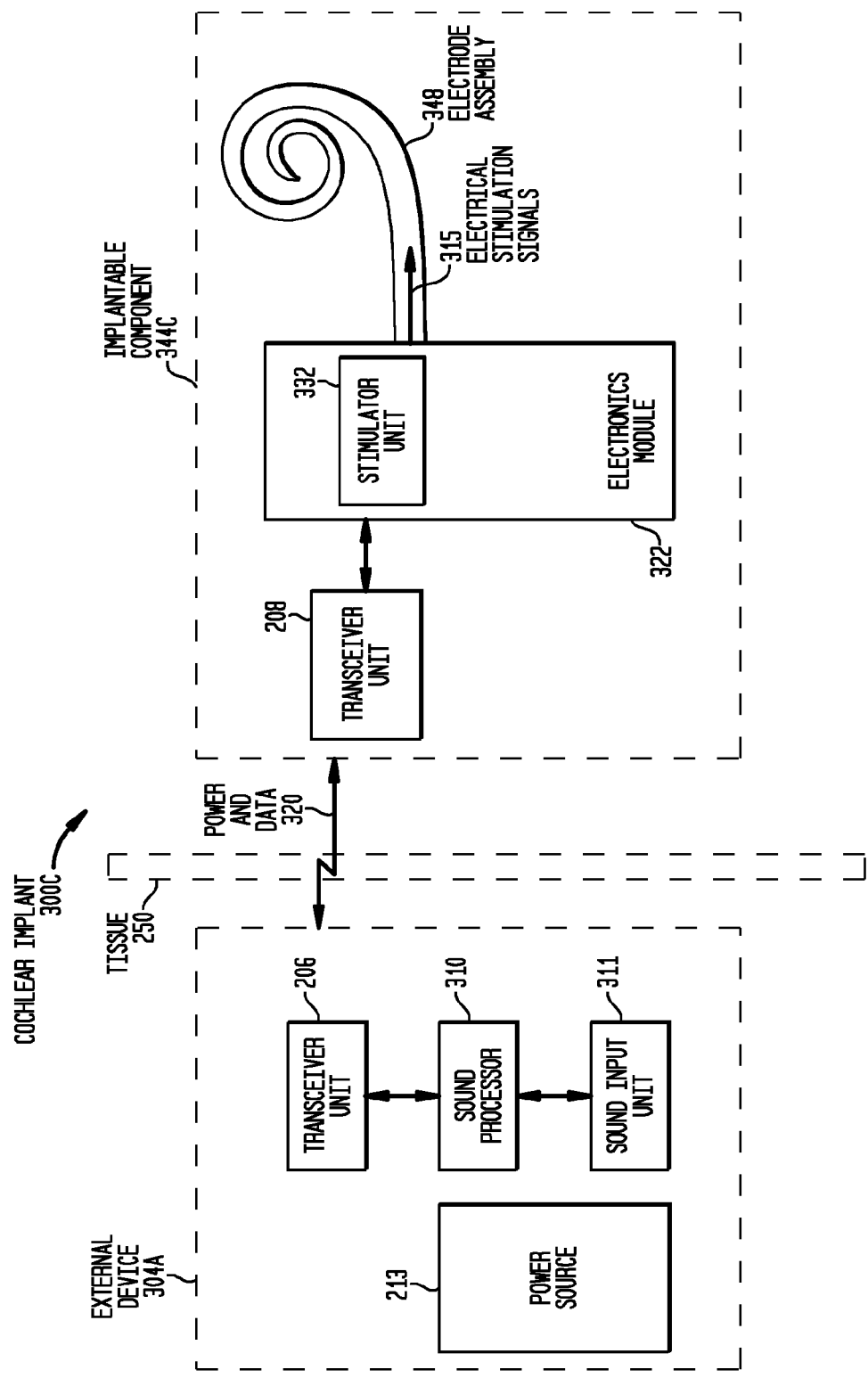
FIG. 3C is yet another alternate functional block diagram of a cochlear implant, in accordance with embodiments of the present invention.

In contrast to the embodiments of FIGS. 3A and 3B, as depicted in FIG. 3C, an embodiment of the present invention of a cochlear implant 300C includes an implantable component 344C that does not include a power storage element 212. In the embodiment of FIG. 3, sufficient power is supplied by external device 304A/304B in real time to power implantable component 344C without storing power in a power storage element. In FIG. 3C, all of the elements are the same as FIG. 3A except for the absence of power storage element 212.

Some of the components of FIGS. 3A-3C will now be described in greater detail.

Figure 4A:
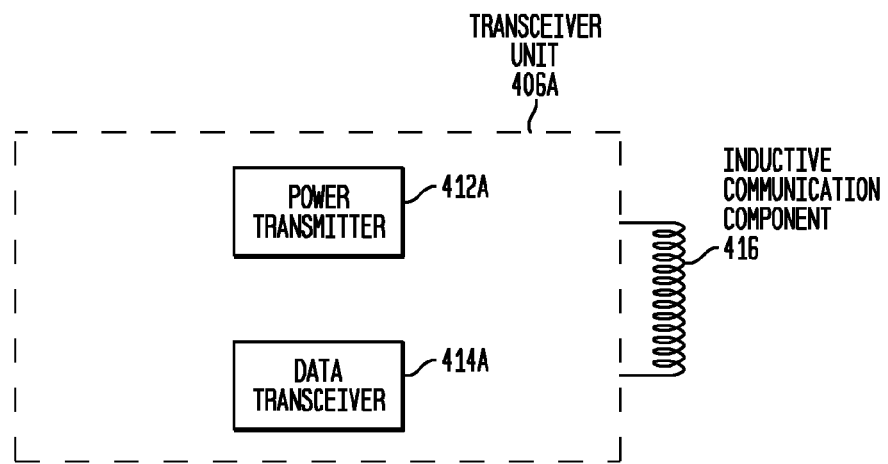
FIG. 4A is a simplified schematic diagram of a transceiver unit of an external device in accordance with embodiments of the present invention.

FIG. 4A is a simplified schematic diagram of a transceiver unit 406A in accordance with an embodiment of the present invention. An exemplary transceiver unit 406A may correspond to transceiver unit 206 of FIGS. 2A-3C. As shown, transceiver unit 406A includes a power transmitter 412a, a data transceiver 414A and an inductive communication component 416 configured to vary its effective coil area, and thus vary the coupling factor k of the system formed by inductive communication component 416 and an implantable.

In an exemplary embodiment, as will be described in more detail below, inductive communication component 416 comprises one or more wire antenna coils (depending on the embodiment) comprised of multiple turns of electrically insulated single-strand or multi-strand platinum or gold wire. Power transmitter 412A comprises circuit components that inductively transmit power from a power source, such as power source 213, via an inductive communication component 416 to implantable component 344A/B/C (FIGS.

3A-3C). Data transceiver 414A comprises circuit components that cooperate to output data for transmission to implantable component 344A/B/C (FIGS. 3A-3C). Transceiver unit 406A may receive inductively transmitted data from one or more other components of cochlear implant 300A/B/C, such as telemetry or the like from implantable component 344A (FIG. 3A).

Transceiver unit 406A may be included in a device that includes any number of components which transmit data to implantable component 334A/B/C. For example, the transceiver unit 406A may be included in a behind-the-ear (BTE) device having one or more of a microphone or sound processor therein, an in-the-ear device, etc.

Figure 4B:
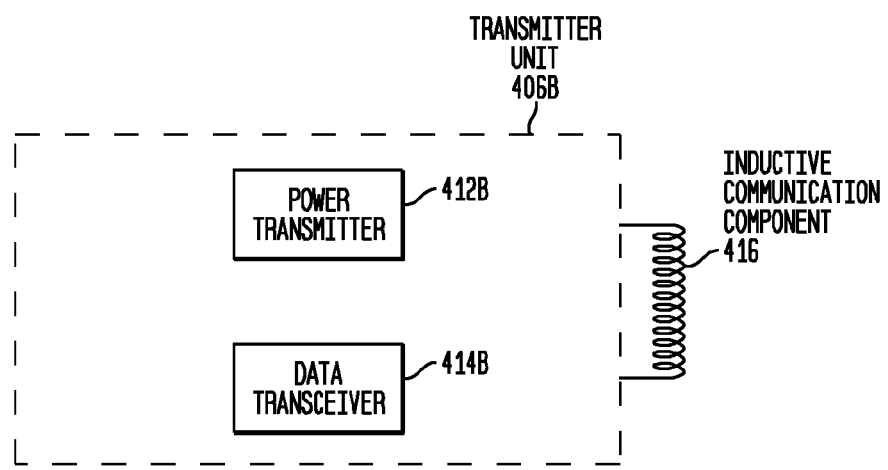
FIG. 4B is a simplified schematic diagram of a transmitter unit of an external device in accordance with embodiments of the present invention.

FIG. 4B depicts a transmitter unit 406B, which is identical to transceiver unit 406A, except that instead of a power transmitter including a power transmitter 412b and a data transmitter 414b.

It is noted that for ease of description, power transmitter 412A and data transceiver 414A are shown separate. However, it should be appreciated that in certain embodiments, at least some of the components of the two devices may be combined into a single device.

It is further noted that while the embodiments depicted in FIGS. 4A and 4B include a communication component configured to vary the effective coil area 416, other embodiments may use a standard coil instead of a communication component configured to vary the effective coil area, at least if a communication component configured to vary the effective coil area is used with the implantable component, 344, depending on the design constraints or goals, as detailed below.

Figure 4C:
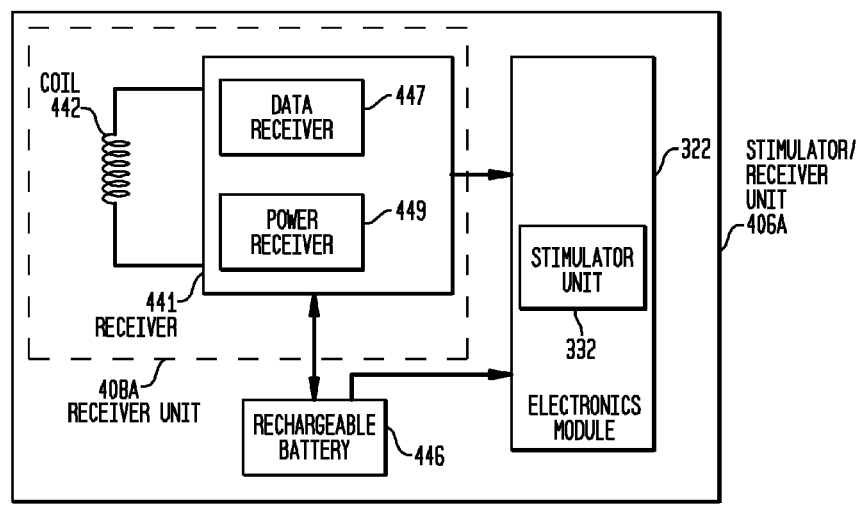
FIG. 4C is a simplified schematic diagram of a stimulator/receiver unit including a data receiver of an implantable device in accordance with embodiments of the present invention.

FIG. 4C is a simplified schematic diagram of one embodiment of an implantable component 444A that corresponds to implantable component 344A of FIG. 3A, except that transceiver unit 208 is a receiver unit. In this regard, implantable component 444A comprises a receiver unit 408A, a power storage element, shown as rechargeable battery 446, and electronics module 322, corresponding to electronics module 322 of FIG. 3A. Receiver unit 408A includes an inductance coil 442 connected to receiver 441. Receiver 441 comprises circuit components which receive via an inductive communication component corresponding to an inductance coil 442 inductively transmitted data and power from other components of cochlear implant 300A/B/C, such as from external device 304A/B. The components for receiving data and power are shown in FIG. 4C as data receiver 447 and power receiver 449. For ease of description, data receiver 447 and power receiver 449 are shown separate. However, it should be appreciated that in certain embodiments, at least some of the components of these receivers may be combined into one component.

In the illustrative embodiments of the present invention, receiver unit 408A and transceiver unit 406A (or transmitter unit 406B) establish a transcutaneous communication link over which data and power is transferred from transceiver unit 406A (or transmitter unit 406B), to implantable component 444A. As shown, the transcutaneous communication link comprises a magnetic induction link formed by an inductance communication component system that includes inductive communication component 416 and coil 442.

The transcutaneous communication link established by receiver unit 408A and transceiver unit 406A (or transmitter unit 406B), in an exemplary embodiment, may use time interleaving of power and data on a single radio frequency (RF) channel or band to transmit the power and data to implantable component 444A. A method of time interleaving power according to an exemplary embodiment uses successive time frames, each having a time length and each divided into two or more time slots. Within each frame, one or more time slots are allocated to power, while one or more time slots are allocated to data. In an exemplary embodiment, the data modulates the RF carrier or signal containing power. In an exemplary embodiment, transceiver unit 406A and transmitter unit 406B are configured to transmit data and power, respectively, to an implantable component, such as implantable component 344A, within their allocated time slots within each frame.

The power received by receiver unit 408A may be provided to rechargeable battery 446 for storage. The power received by receiver unit 408A may also be provided for and distribution, as desired, to elements of implantable component 444A. As shown, electronics module 322 includes stimulator unit 332, which in an exemplary embodiment corresponds to stimulator unit 322 of FIGS. 3A-3C, and may also include one or more other functional components used to generate or control delivery of electrical stimulation signals to the recipient.

In an embodiment, implantable component 444A comprises a receiver unit 408A, rechargeable battery 446 and electronics module 322 integrated in a single implantable housing, referred to as stimulator/receiver unit 406A. It would be appreciated that in alternative embodiments, implantable component 344 may comprise a combination of several separate units communicating via wire or wireless connections.

Figure 4D:
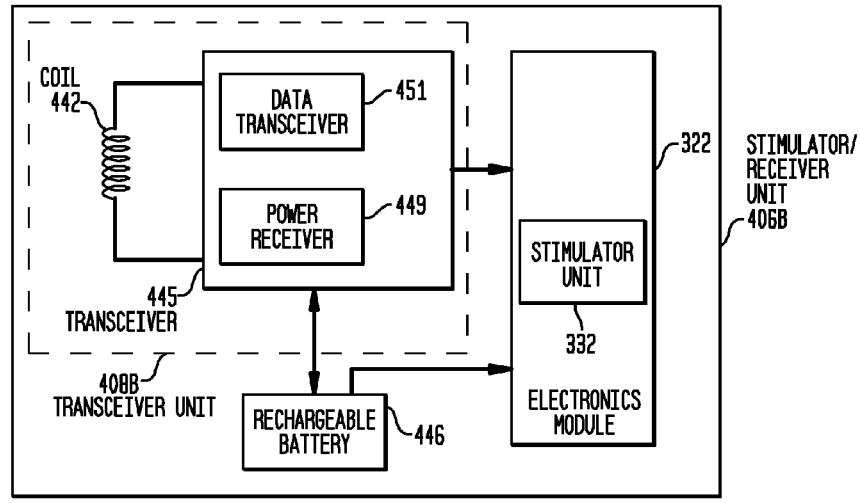
FIG. 4D is a simplified schematic diagram of a stimulator/receiver unit including a data transceiver of an implantable device in accordance with embodiments of the present invention.

FIG. 4D is a simplified schematic diagram of an alternate embodiment of an implantable component 444B. Implantable component 444B is identical to implantable component 444A of FIG. 4C, except that instead of receiver unit 408A, it includes transceiver unit 408B. Transceiver unit 408B includes transceiver 445 (as opposed to receiver 441 in FIG. 4C). Transceiver unit 445 includes data transceiver 451 (as opposed to data receiver 447 in FIG. 4C).

Figure 4E:
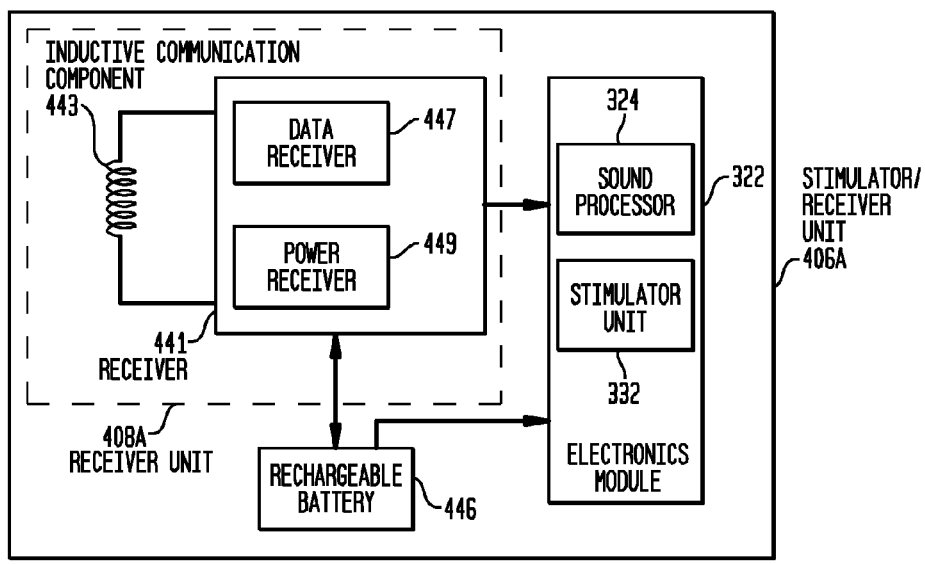
FIG. 4E is a simplified schematic diagram of a stimulator/receiver unit including a data receiver and a communication component configured to vary the effective coil area of an implantable device in accordance with embodiments of the present invention.
Figure 4F:
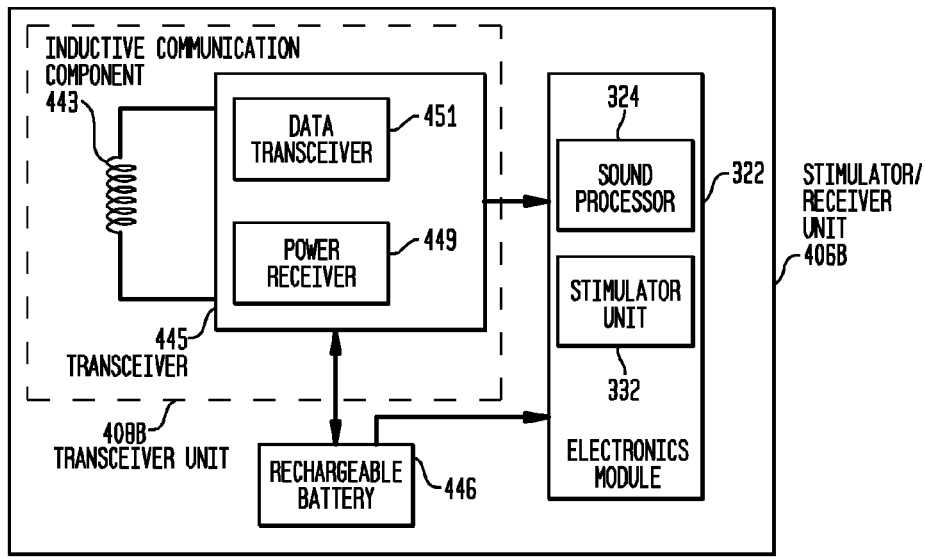
FIG. 4F is a simplified schematic diagram of a stimulator/receiver unit including a data transceiver and a communication component configured to vary the effective coil area of an implantable device in accordance with embodiments of the present invention.

FIGS. 4E and 4F depict alternate embodiments of the implantable components 444A and 444B depicted in FIGS. 4C and 4D, respectively. In FIGS. 4E and 4F, instead of coil 442, implantable components 444C and 444D (FIGS. 4E and 4F, respectively) include inductive communication component 443. Inductive communication component 443 is configured to vary the effective coil area of the component, and may be used in cochlear implants where the exterior device 304A/B does not include a communication component configured to vary the effective coil area (i.e., the exterior device utilizes a standard inductance coil). In other respects, the implantable components 444C and 444D are substantially the same as implantable components 444A and 444B. Note that in the embodiments depicted in FIGS. 4E and 4F, the implantable components 444C and 444D are depicted as including a sound processor 342. In other embodiments, the implantable components 444C and 444D may not include a sound processor 342.

In describing the embodiments of the present invention, reference has been made to an inductive communication component configured to vary the effective coil area of the component. Specifically, embodiments of exterior device 304A/B and/or implantable component 344C/D of a cochlear prosthesis may include a communication component configured to vary the effective coil area of the component. Some exemplary embodiments of communication components configured to vary the effective coil area of the component will now be discussed.

Herein, unless otherwise specified, the term "coil" refers to an inductance coil. Inductance coils permit power to be transferred from one coil to another coil by magnetic inductance. In the embodiments described herein, the coils are separated by a layer of tissue, referred to as skin flap. In an embodiment, the coil located external to the recipient (e.g., the coil that is part of the external device 204) is in electrical communication with a power supply (e.g., a battery), and that coil induces a current in the coil implanted in the recipient (e.g., the coil that is part of the internal component 208). The external coil and the internal coil are collectively referred to herein as the inductance communication component system. Performance characteristics of the inductance communication component system include the current and voltage that may be supplied to the implanted component by the external device via magnetic induction across the coils for a given power supply of the external device. More specifically, performance characteristics of the inductance communication component system includes the implant voltage, which is the voltage generated over the inductance communication component system by alternating flux generated by the external coil.

Figure 5:
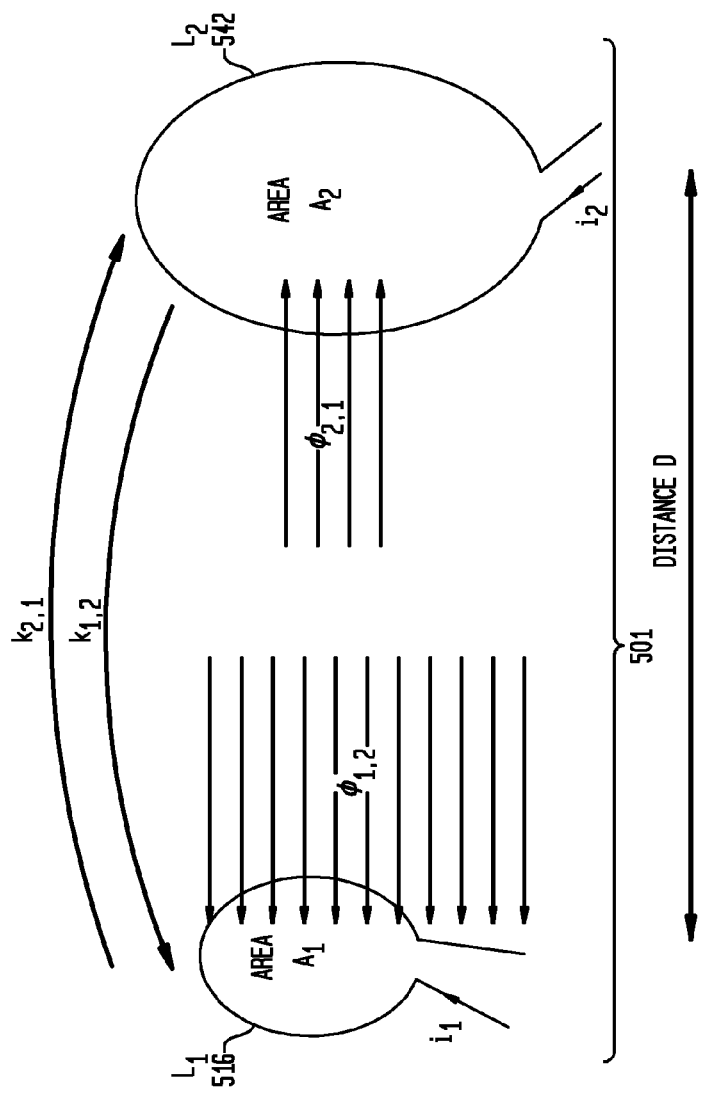
FIG. 5 is a simplified schematic diagram depicting flux in an inductance communication component system.

The performance characteristics of the inductance coils used in the present invention vary based on the distance between the coils and the area enclosed by the wire loops of the inductance coils. In this regard, FIG. 5 depicts a functional schematic of an inductance communication component system 501 including external coil 516, designated $L_1$, and implantable coil 542, designated $L_2$, in FIG. 5. As may be seen in FIG. 5, the area $A_1$ of the external coil 516 is less than the area $A_2$ of the implantable coil 542. In the inductance communication component system of FIG. 5, the two coils are aligned substantially parallel to each other (i.e., the plane in which the looped wires of the coils substantially lie are substantially parallel to one another), concentric with each other, and are separated by a distance D (taken from the planes in which the loop wires of the coils substantially lie). The distance D typically includes the thickness of the tissue between the two coils, the thickness of casing walls located between the two coils, if the coils are encased in a plastic material or the like, and hair and/or clothing or any other material that may be interposed between the two coils. The areas enclosed by the coils may be calculated by calculating the mean diameter of the wire loops of the coils (e.g., if the coil includes three loops, the diameter of each of the loops is summed and the result is divided by three), and using this mean diameter in calculating the area.

FIG. 5 depicts magnetic inductive flux, $\phi$, between the external coil 516 (coil L1) and the implantable coil 542 (coil L2). In FIG. 5, external coil 515 and implantable coil 542 have mutual coupling factors here represented as $k_{21}$ and $k_{12}$.

The coupling factor k increases or decreases in relation to the ratio of the areas enclosed by the coils and the distance D between the coils. In a simplified model of an inductance communication component system, the magnetic field between the coils is considered homogeneous, and the effects of bending and flux cancellation by the closed magnetic field lines are excluded. Also, the distance D separating the coils may be assumed to be much smaller than the respective mean radiuses of the coils.

In the exemplary system of FIG. 5, the coupling factor k is defined as $k^2 = k_{12} \times k_{21}$, where $k_{12} = L_{12}/L_{11}$ and $k_{21} = L_{21}/L_{22}$. If $L_{12} = L_{21}$, the expression $k = L_{12}/\sqrt{(L_{11} \times L_{22})}$ is obtained. In the case of mutual inductance, $L_{21} = L_{12}$. Further, $L_{11}$ and $L_{22}$ are the self-inductances of $L_1$ and $L_2$, respectively, and $L_{12}$ and $L_{21}$ are the mutual inductances between $L_1$ and $L_2$. It is noted that k is not to be greater than one.

In view of the above analysis, it can be seen that the coupling factor k may be considered independent of the current going into the coils, and may be considered dependent on the area enclosed by the inductance coils. An embodiment of the present invention relies on this phenomenon, as will become apparent below, by utilizing an inductive communication component configured to vary the effective coil area of the component. The phrase "inductive communication component configured to vary the effective coil area of the component" as used herein refers to a component configured to inductively transmit and/or receive power and or data. In an embodiment, this inductive communication component may be configured to vary the effective coil area of the component. For example, in an embodiment, the inductive communication component may comprise two coils each of different diameters (and thus effective coil areas), where the coils may be selectively used, thereby varying the effective coil area of the inductive communication component. By varying the effective coil area, the coupling factor k between the coils may be varied, as will be discussed in more detail below.

Figure 6:
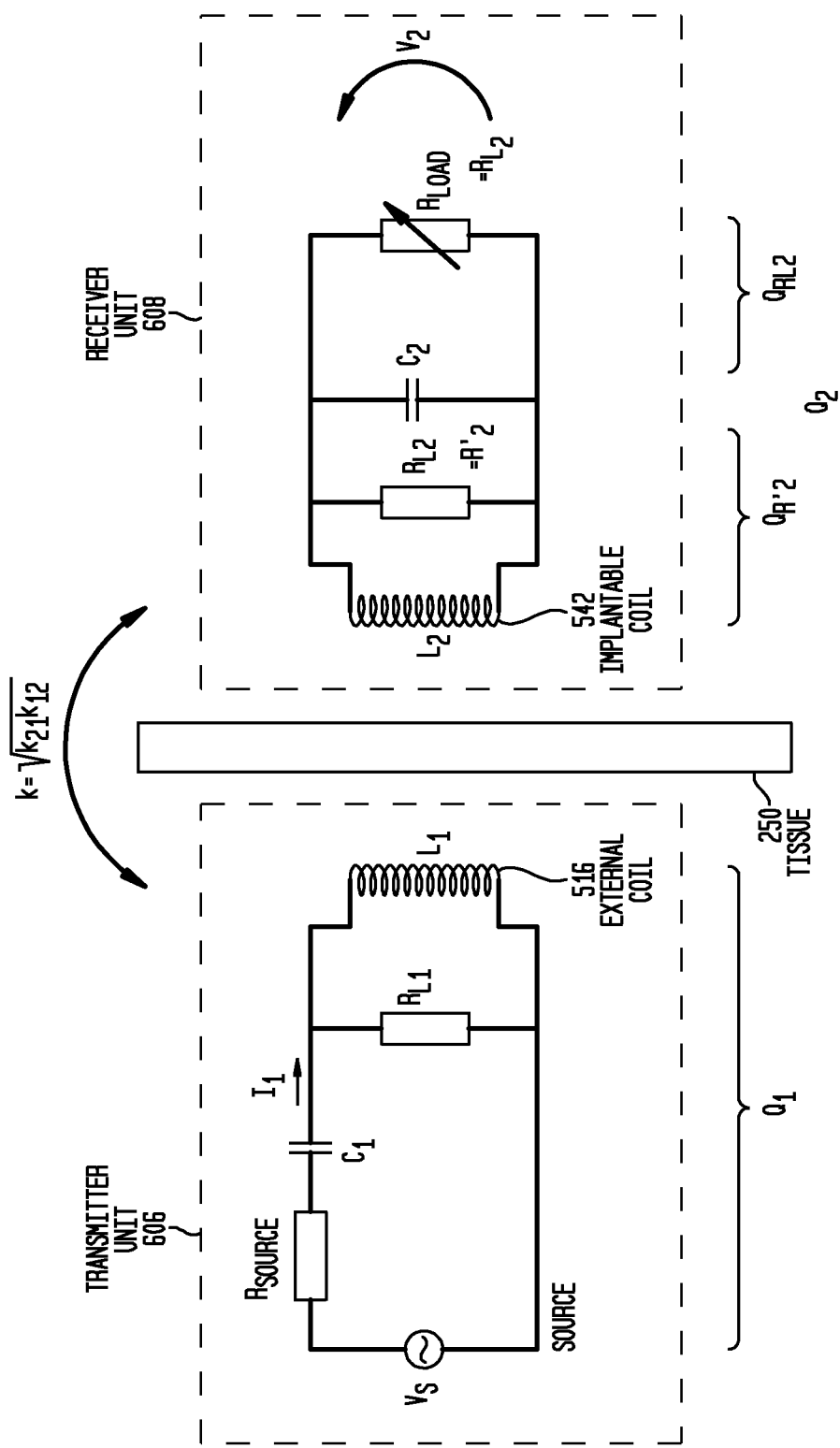
FIG. 6 is a simplified circuit diagram of a transmitter unit of an external device and a receiver unit of an implantable device in accordance with embodiments of the present invention.

FIG. 6 presents a high level circuit diagram of in a transmitter unit 606 of an external device and a receiver unit 608 of an implantable component. FIG. 6 will be used to further explain the concept of power and/or data transmission via magnetic inductance. External coil 516 and implantable coil 542 are inductively coupled to one another across tissue 250. The external coil 516 is in series resonance with capacitor $C_1$, and implanted coil is in parallel resonance with capacitor $C_2$ at or close to the magnetic inductance operating frequency of the inductance communication component system. The implant load $R_{L2}$ may be variable, depending on, for example, in the case of a cochlear implant, the selected stimulation strategy (e.g., monopolar or bipolar electrode stimulation methods at different pulse rates), or the charging cycle of the rechargeable battery in the implantable component (e.g., a lithium ion battery may be recharged over two consecutive different charging phases). Still further, $R_{L2}$ may vary as a result of a failure of the rechargeable battery in the implantable component, such as when, for example, the implantable component must operate in the so-called fall-back mode (e.g., where power to drive the electrodes is supplied at approximately a one to one ratio of instantaneous power used by the implantable component to instantaneous power supplied via magnetic induction to the implantable component).

If the implant load $R_{L2}$ varies significantly, the performance characteristics of the inductance communication component system may be negatively impacted. By way of example only, if the implant load becomes too high the ability of external coil 516 to supply power to implantable coil 542 via magnetic induction becomes degraded, at least in the scenario where the effective coil area of the external coil 516 is substantially different (e.g. smaller coil radius) than the effective coil area of the implantable coil 542. An inductive communication component configured to vary the effective coil area of the component may be utilized to at least limit the negative impact on performance characteristics in such an eventuality. In implantable systems, same effective coil areas may lead to an over-coupling. That is, while not represented in the above-equations, which were arrived at based on a simplified model of transcutaneous power transfer via magnetic induction, k may vary with varying distance between two coils having the same effective coil area. Thus, an embodiment of the present invention utilizes an inductive communication component configured to vary the effective coil area of the component to adjust the coupling factor k, and thereby adjust the performance characteristics of the inductance communication component system. While the distance D between the coils may also be varied to adjust the coupling factor k, in implants, the distance D is typically a fixed value based on the fact that the skin flap thickness cannot be changed. Accordingly, embodiments of the present invention focus on changing the effective coil area of the inductive communication component(s).

Assuming skin flap thickness is constant, the power link efficiency for an inductive coil system may be approximated by the following equations:

$$\eta_{pr \to sec} = \frac{k^2 Q_1 Q_2}{(1-k^2)^2 + k^2 Q_1 Q_2} \quad \text{(Equation 1)}$$

$$\eta_{link} = \eta_{pr \to sec} \cdot \eta_{sec \to R_L} = \frac{k^2 Q_1 Q_2}{(1-k^2)^2 + k^2 Q_1 Q_2} \frac{Q_{R'_2}}{Q_{R_{L2}} + Q_{R'_2}} \quad \text{(Equation 2)}$$

$$\eta_{link} = \eta_{pr \to sec} \cdot \eta_{sec \to R_{L2}} = \quad \text{(Equation 3)}$$

$$\frac{k^2 Q_1 \frac{Q_{R_{L2}} \cdot Q_{R'_2}}{Q_{R_{L2}} + Q_{R'_2}}}{(1-k^2)^2 + k^2 Q_1 \frac{Q_{R_{L2}} \cdot Q_{R'_2}}{Q_{R_{L2}} + Q_{R'_2}}} \frac{Q_{R'_2}}{Q_{R_{L2}} + Q_{R_2}} =$$

$$\frac{k^2 Q_1 Q_{R_{L2}} Q^2_{R'_2}}{((1-k^2)^2 (Q_{R_{L2}} + Q_{R'_2}) + k^2 Q_1 Q_{R_{L2}} Q_{R'_2}) Q_{R_{L2}} + Q_{R'_2}}$$

where:
$\eta_{link}$=link efficiency
$Q_1$=loaded Q factor of the external coil
$Q_2$=loaded Q factor of the implant coil
$Q_{R'2}$=unloaded Q factor of the implant coil
$Q_{RL2}$=Q factor contribution by the load RL
k=coupling factor of the coils
The quality factors Q are those related to the magnetic inductance operating frequency.

Equation 3 shows an optimum for:

$$Q_{R_{L2},opt} \approx Q_{R'_2} \frac{1}{\sqrt{1 + k^2 Q_1 Q_{R'_2}}} \quad \text{(Equation 4)}$$

The critical coupling factor may be defined as:

$$k_{crit} = \sqrt{\frac{1}{Q_1 Q_2}} \quad \text{(Equation 5)}$$

As may be seen from the above analysis, the efficiency of a magnetic inductance link is dependent on the coupling factor k. Because the magnetic coupling factor k and distance D between coils of an inductance communication component system (D varies due to, for example, skin flap thickness) are directly related to each other, it is noted that the voltage of an implantable component may vary from recipient to recipient. It is further noted that from Equation 4, the external coil may be selected with a coupling factor k to obtain the most optimal load value $Q_{RL2}$, where $Q_{RL2} = \omega C_2 R_{L2}$).

It is noted that the above equations are based on an assumption that the coupled flux is a linear function of the magnetic field density ø and area A. This result is valid for relatively small inter-coil distances D, and A2>A1 (in some embodiments, A1 may be between 50% to 90% of A2). Note also that in developing the above equations, k has been assumed to be independent of the number of windings/turns.

With reference to FIGS. 5 and 6 and the above equations, overcritical coupling occurs when the product of the loaded Q factor of the external coil and the loaded Q factor of the implant coil is high. A large voltage drop occurs when k>>$k_{crit}$. To avoid large voltage drops or variations in the implant, the coupling factor k may be varied (e.g., decreased when k>>$k_{crit}$) by changing the radius or diameter of the external or implanted coils, where relationship between the coupling factor k and the coil area configuration has been described above with respect to FIG. 5.

If it is assumed that the magnetic field is homogeneous and the effects of bending and flux cancellation are excluded, as noted above, and if it is also assumed that the distance D is much smaller than the coil radius, the following equations may further be developed:

$$k_{12} = \frac{L_{12}}{L_{11}} = \frac{\phi_{12}/i_2}{\phi_{11}/i_1} \quad \text{(Equation 6)}$$

$$k_{21} = \frac{L_{21}}{L_{22}} = \frac{\phi_{21}/i_1}{\phi_{22}/i_2} \quad \text{(Equation 7)}$$

As noted above, $k^2 = k_{12} \times k_{21}$. This equation may be rewritten as $$k^2 = k_{12} k_{21} = \frac{\phi_{12} \phi_{21} i_1 i_2}{\phi_{11} \phi_{22} i_1 i_2} = \frac{\phi_{12} \phi_{21}}{\phi_{11} \phi_{22}} \quad \text{(Equation 8)}$$

Equation 8 shows that the coupling factor k is independent of the current going into the windings of the external (primary) coil and/or implantable (secondary) coil. The magnetic field density B generated by a coil is the ratio of the generated total flux to the area A enclosed by its windings. Accordingly Equation 8 could be rewritten as:

$$k = \sqrt{\frac{\phi_{12} \phi_{21}}{\phi_{11} \phi_{22}}} \quad \text{(Equation 9)}$$

and therefore $$k_{D \approx 0, A_2 \geq A_1, \text{no flux cancelation}} \approx \sqrt{\frac{B_2\left(\frac{A_1}{A_2}\right) A_1 \cdot B_1\left(\frac{A_1}{A_2}\right) A_2}{B_1 A_1 \cdot B_2 A_2}} = \sqrt{\frac{A_1^2}{A_2^2}} = \frac{A_1}{A_2} \quad \text{(Equation 10)}$$

Accordingly, from equation 10, it can be seen that varying the effective coil area of the inductive communication component(s) may vary the coupling factor k.

It is noted that the above-equations provide a simplified way of calculating the coupling factor k. However, in other embodiments of the present invention, the coupling factor k may be calculated or otherwise determined using different equations (e.g., elliptic integrals), empirically and/or through computational analysis. Such alternate calculations/determinations may be utilized to take into account factors that were considered to have no meaningful impact on the coupling factor k in the simplified equations above.

An exemplary embodiment includes an inductance communication component system usable in a transcutaneous inductance communication system where the external coil has about 70%, 60%, 50% or 40% of the effective coil area of the corresponding implantable coil. A transcutaneous inductance link where the coupling factor k is substantially lower than 1 is usable with some exemplary embodiments. An exemplary embodiment includes an inductance communication component system where the coupling factor k is about 0.7, 0.6, 0.5, 0.4, 0.3 or 0.2. Such exemplary embodiments may be usable, by way of example only, in transcutaneous inductance links where the distance D between the coils is about 1.5 to 12 mm.

In this regard, it has been determined that in transcutaneous inductance links where the skin flap thickness is relatively small (e.g., about 1.5 to 3 mm), the voltage of an implantable component, such as a receiver stimulator of a cochlear implant, measured at the implanted coil, may be substantially lower (e.g., about 30%, 40%, 50% or 60%) than the voltage of a similarly situated transcutaneous inductance link where the skin flap thickness is greater (e.g., about 6 or more). Utilizing an inductance communication component system where the external coil (the primary coil) has an effective coil area that is substantially smaller than that of the implantable coil (the secondary coil), the voltage of the implantable component will be higher when used with a substantially low skin flap thickness. This as compared to a similarly situated transcutaneous inductance link where the coils have an effective coil area that is about the same. It is believed that in an exemplary embodiment, the fact that the external coil has a smaller effective coil area than that of the implantable coil alleviates, at least to some extent, the effects of reflective resistance from the implantable component, at least in scenarios where the implantable coil is in electrical communication with a component that has a relatively high load voltage (e.g., 11-12 V). Accordingly, varying the effective coil area of an inductance coil has utility because such action may overcome the phenomenon of reflective resistance, thereby improving the efficiency of the inductive link between the external coil 516 and the implantable coil 542.

Figure 7:
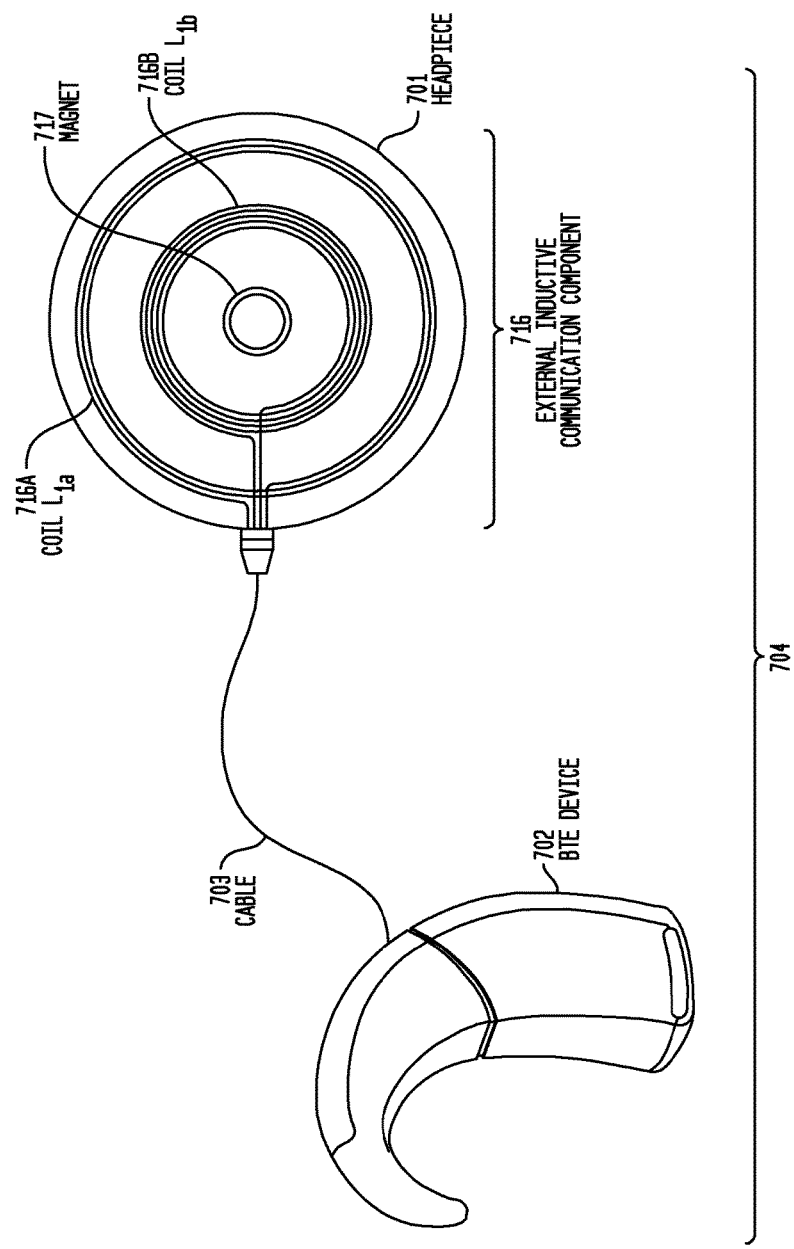
FIG. 7 is a simplified schematic diagram of an external device including a communication component configured to vary the effective coil area in accordance with embodiments of the present invention.

FIG. 7 illustrates an exemplary inductive communication component 716 configured to vary the effective coil area of the component according to an embodiment of the present invention. As illustrated, an external device 704 of a cochlear implant prosthesis comprises, included in headpiece 701, an external inductive communication component 716 configured to vary the effective coil area of the component. In an exemplary embodiment, the external device 704 is configured to transmit magnetic inductance power transcutaneoulsy via external inductive communication component 716 to an implantable component including an inductance coil. Inductive communication component 716 is electrically coupled to behind-the-ear (BTE) device 702 via cable 703. BTE device 702 may include, for example, at least some of the components of the external device 304A or 304B. It is noted that external device 704 may have some or all of the same components as the external devices of FIGS. 2A-3C detailed above.

Figure 8B:
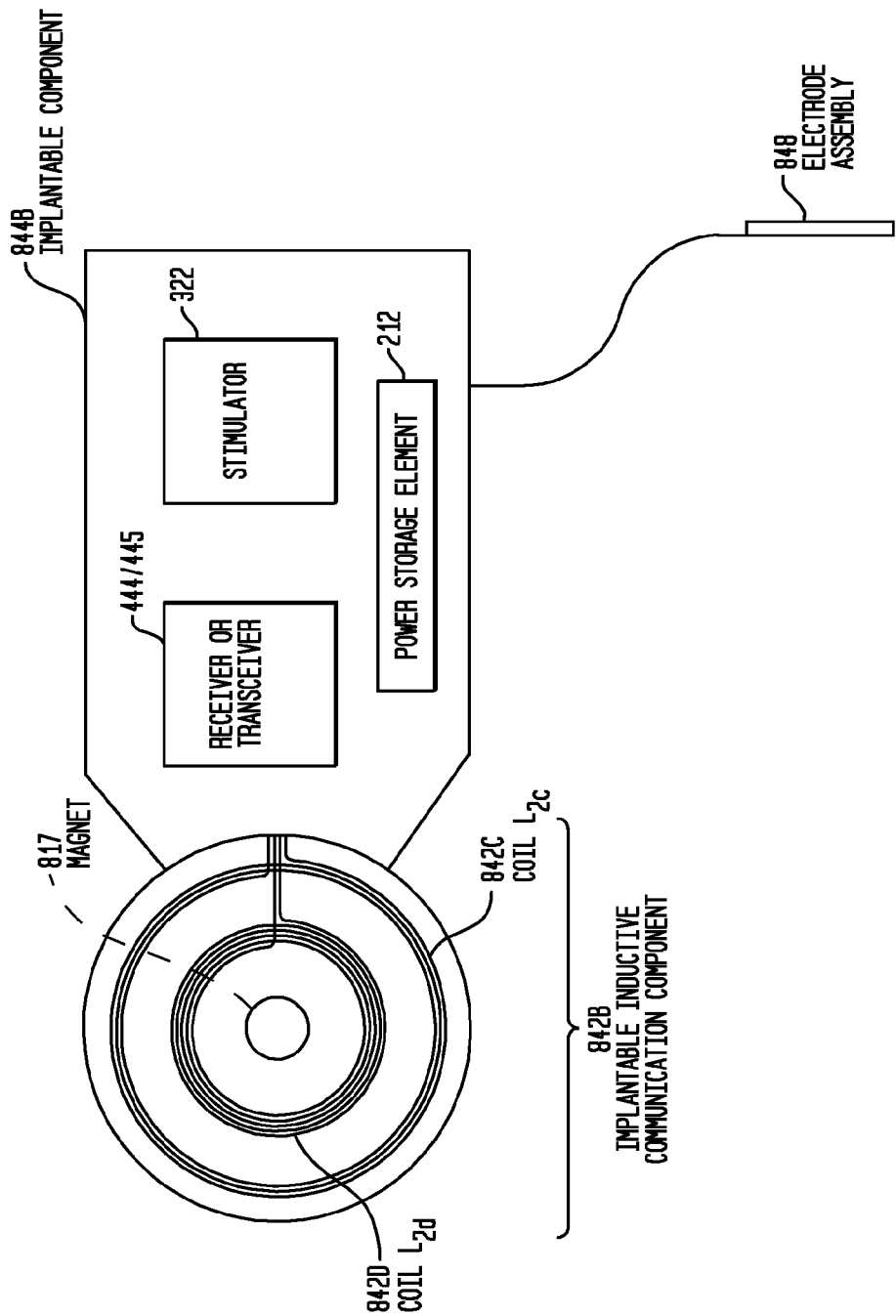
FIG. 8B is a simplified schematic diagram of an implantable component including a communication component configured to vary the effective coil area in accordance with embodiments of the present invention.

FIG. 8A illustrates an exemplary embodiment of an implantable component 844A, which may be a receiver/stimulator of a cochlear implant, and includes an implantable coil 842A that is a standard coil, and a power consuming apparatus, such as, for example, a power storage element 212 in the form of a rechargeable battery, and/or a stimulator 322 configured to provide electrical current to electrode assembly 848, as will be described in greater detail below. Implantable coil 842A is a standard coil and is configured to receive at least a portion of the magnetic inductance power transmitted from the external device via the implantable coil to power the power consuming apparatus of the implantable component 844A. As will be described in more detail below with respect to FIG. 8B, embodiments of an implantable component corresponding to a receiver/stimulator of a cochlear implant may include an implantable inductive communication component configured to vary the effective coil area of the component.

It is noted that the embodiments of FIGS. 8A and 8B may include some or all of the components of the implantable devices of FIGS. 2A-3C and 4C-4F.

Referring back to FIG. 7, the external inductive communication component 716 comprises coil 716A and coil 716B. As may be seen, the loops of coil 716A encircle the loops of coil 716B. The loops of both coils encircle magnet 717 that is used to hold the headpiece, and thus the external inductive communication component 716 against the head of a recipient when a ferrous material has been implanted in the head of the recipient. Coil 716A has an effective coil area (i.e., the value of the area determined by taking the median of the areas encompassed by the individual loops of coil 716A) that is greater than the effective coil area of coil 716B (i.e., the value of the area determined by taking the median of the areas encompassed by the individual loops of coil 716B). By selecting coil 716A or coil 716B to induce a magnetic inductance current into coil 842 of implantable component 844A, the effective coil area of the external inductive communication component 716 may be varied, because the effective coil areas of coil 716A and coil 716B are different, as may be seen from FIG. 7.

Coil 716A and coil 716B are electrically isolated from one another. By electrically isolated, it is meant that the wire loops of one coil are not in electrical communication with the wire loops of the other coil. By way of example, the coils 716A and 716B may be formed from two separate wires, and electrical insulation and/or sufficient spacing is interposed between the two separate wires at locations where the wires may cross.

Coil 716A and coil 716B are variously selected to induce a magnetic inductance current into implantable coil 842A. This may be done, for example, through the use of switches to variously place the respective coils into electrical communication with a power source.

It is noted that in an exemplary embodiment of the present invention, an external inductive communication component may vary the effective coil area by physically changing the diameter of a single coil, in lieu of or in addition to selecting between coils of different effective coil area. Such an embodiment is described in more detail below with respect to FIG. 9.

Figure 10:
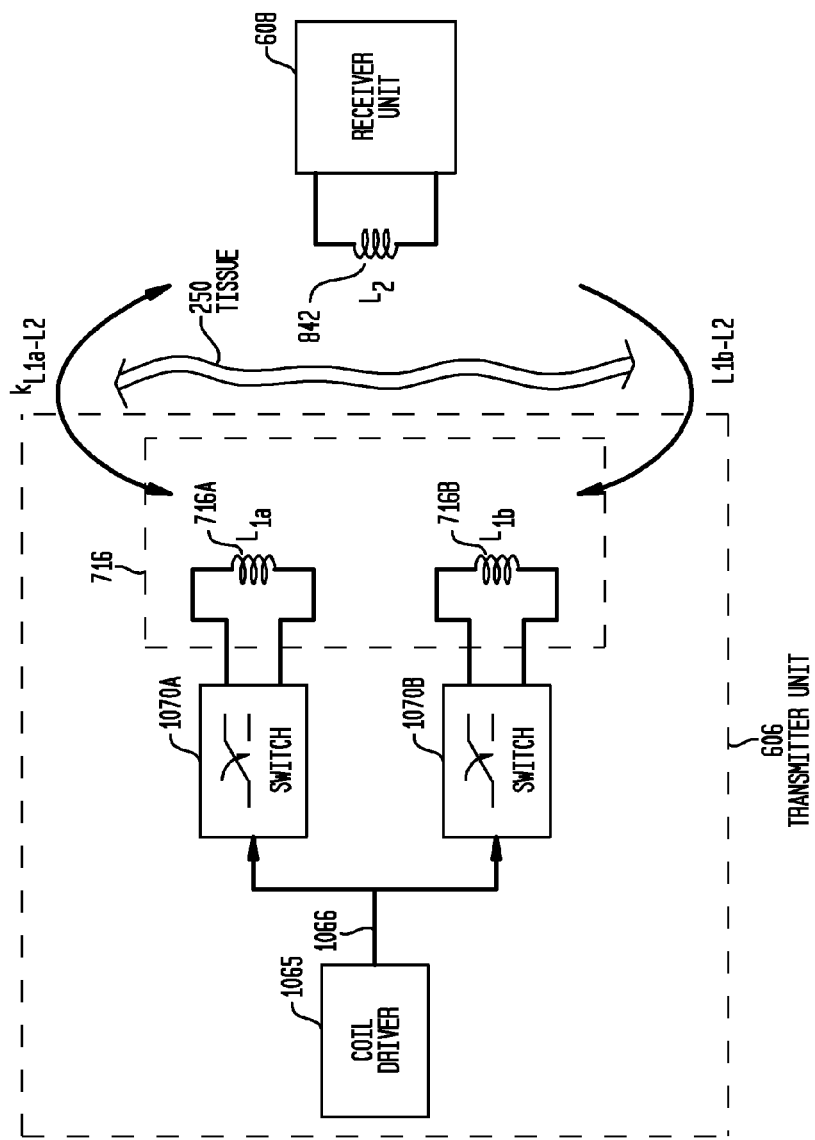
FIG. 10 is a simplified circuit diagram of a transmitter unit of an external device and a receiver unit of an implantable component in accordance with embodiments of the present invention.

FIG. 10 illustrates an exemplary transmitter unit 606 that includes a coil driver 1065, corresponding to a power source, that outputs power via power line 1066. Switches 1070A and 1070B are used to alternately place coil 716A and 716B into electrical communication with power line 1066, and thus coil driver 1065. Accordingly, if coil 716A is placed into electrical communication with coil driver 1065, and coil 716B is not in electrical communication with coil driver 1065, coil 716A functions as an inductance coil, and visa-versa. If coil 716A is in electrical communication with coil driver 1065, and coil 716B is not in electrical communication with coil driver 1065, external inductive communication component 716 has an effective coil area of the effective coil area of coil 716A. If coil 716B is in electrical communication with coil driver 1065, and coil 716B is not in electrical communication with coil driver 1065, the external inductive communication component 716 has an effective coil area of the effective coil area of coil 716B, and coil 716B functions as an inductance coil. Thus, through the use of switches 1070A and 1070B, external inductive communication component 716 is configured to vary the effective coil area of the component.

An exemplary embodiment of the external inductive communication component 716 of FIG. 7 is such that coil 716A has a mean diameter of about 24 mm to 30 mm (corresponding to an effective coil area of about 452 mm$^2$ to 709 mm$^2$) In this exemplary embodiment, coil 716B has a mean diameter of about 20-28 mm (about 314 mm$^2$ to 615 mm$^2$), and the magnet 717 is about 10 mm in diameter. A further exemplary embodiment of the external inductive communication component 716 of FIG. 7 is such that when used with an implantable coil, the external inductive communication component has about 70%, 60%, 50% or 40% of the effective coil area of the corresponding implantable coil.

Figure 11:
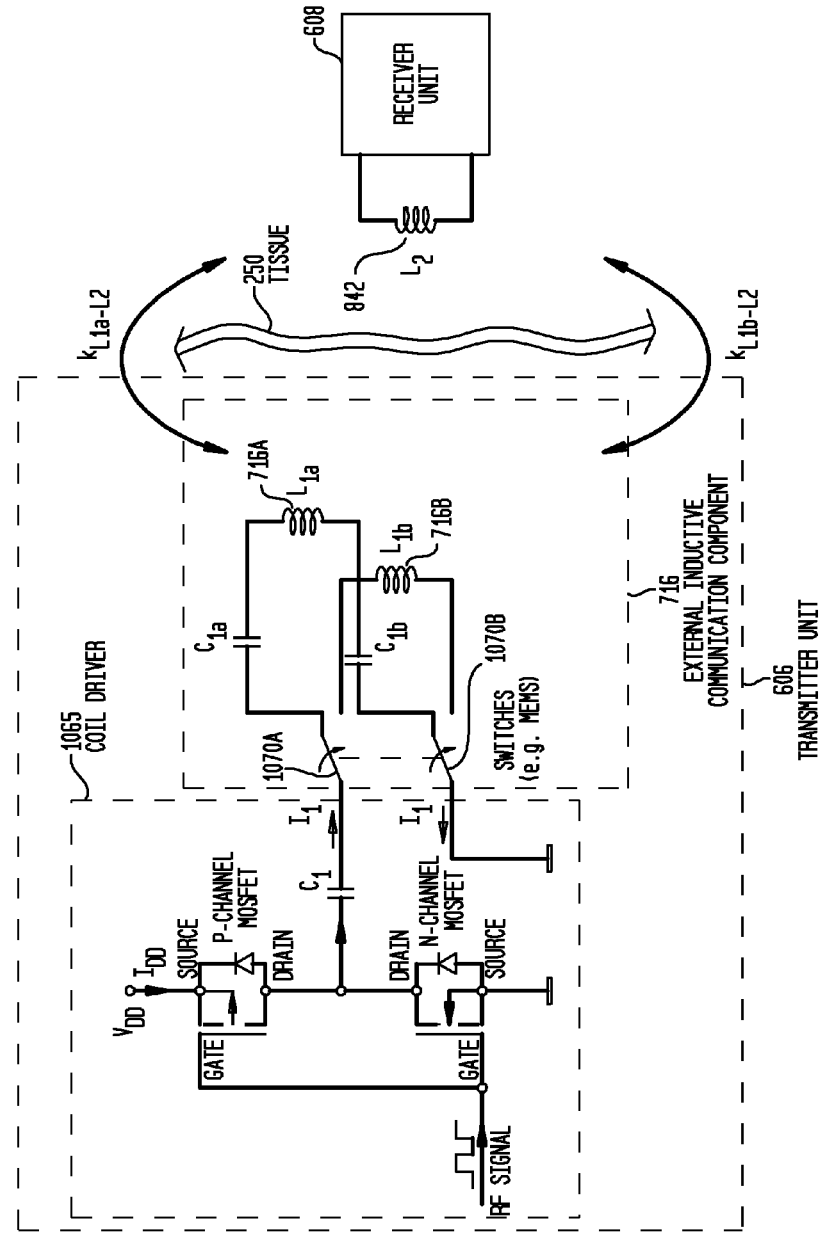
FIG. 11 is a more-detailed circuit diagram of the transmitter unit of an external device and a receiver unit of an implantable component of FIG. 10.

FIG. 11 presents additional details of the embodiment depicted in FIG. 10, including details of the coil driver 1065 and circuit components, such as capacitors $C_{1a}$ and $C_{1b}$ located between the external coils 716A and 716B and the coil driver 1065. As may be seen, the coil driver includes capacitor $C_1$ and diodes arranged in a MOSFET circuit to drive the coils based on the received RF signal from other components of the external device, such as, for example, the RF signal outputted by a sound processor. It is noted that in an embodiment of the present invention utilizing two coils, such as that depicted in FIG. 10 (or FIG. 12, described in greater detail below), the self-inductance values of coil 716A and 716B ($L_{1a}$ and $L_{1b}$, respectively), are relatively close together, or chosen to maintain the same value of the capacitive series tuning element $C_1$. In an exemplary embodiment, this may be accomplished by adding more windings to coil 716B as compared to coil 716A. Alternatively, or in addition to this, variations between the self-inductances of the coils may be compensated for by using $C_{1a}$ and $C_{1b}$ instead of $C_1$.

As noted above, while the implantable component 844A of FIG. 8A utilizes a standard coil, an embodiment of the present invention includes an implantable component that includes an inductive communication component configured to vary the effective coil area of the component. In this regard, referring to FIG. 8B, there is an implantable component 844B corresponding to a receiver/stimulator of a cochlear implant, that includes an implantable inductive communication component 842B configured to vary the effective coil area of the component. In an exemplary embodiment, the implantable inductive communication component 842B includes coil 842C and separate coil 842D. As may be seen, the loops of coil 842C encircle the loops of coil 842D. Both coils encircle a magnet 817 or another suitable ferrous material. The magnet 817 permits an exterior coil to be aligned with the implantable inductive communication component 844B. Coil 842C has an effective coil area that is greater than the effective coil area of coil 842D. By selecting coil 842C or coil 842D to be in electrical communication with a load, and thus use the magnetic inductance current from external device 704 (which may include a standard coil instead of the inductive communication component 716 described above) to power a power consuming apparatus in the implantable component 844B, the effective coil area of coil 842B may be varied, because the effective coil areas of coil 842C and 842D are different, as may be seen from FIG. 8B.

Figure 12:
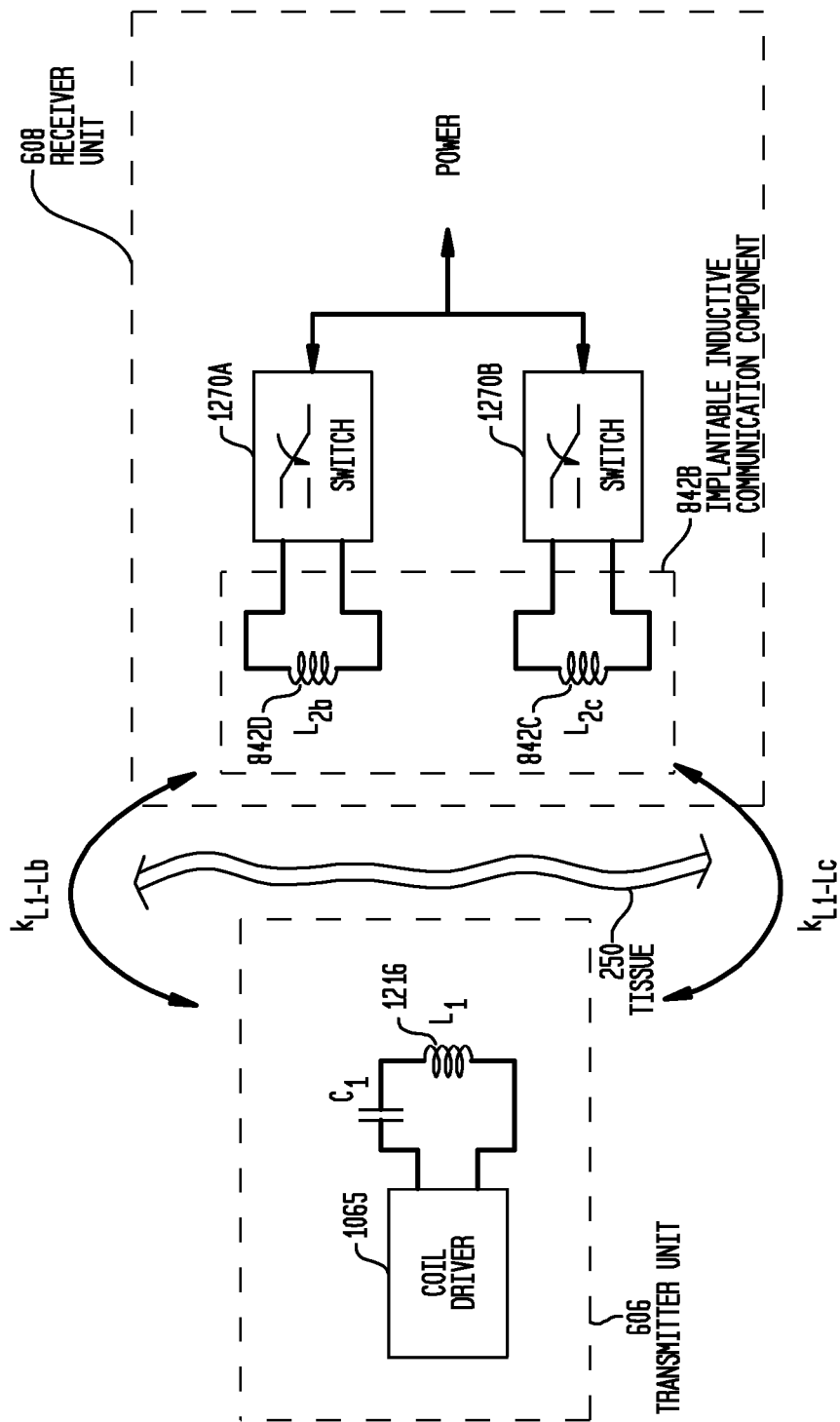
FIG. 12 is an alternate simplified circuit diagram of a transmitter unit of an external device and a receiver unit of an implantable component in accordance with embodiments of the present invention.

Coil 842C and coil 842D are electrically isolated from one another. Coil 842C and coil 842D may be variously selected to be in electrical communication with a load of the implantable component 844B. This may be done, for example, through the use of switches to variously place the respective coils into electrical communication with a source of power. In this regard, FIG. 12 depicts an exemplary receiver unit 808 that includes switches 1270A and 1270B that are used to alternately place coil 842C and 842D into electrical communication with a load of the implantable component in which the receiver unit 608 is located. Accordingly, if coil 842C is placed into electrical communication with a load of the implantable component, and coil 842D is not in electrical communication with a load, coil 842C functions as an inductance coil, and visa-versa. If coil 842C is in electrical communication with a load, and coil 842C is not in electrical communication with a load, implantable inductive communication component 842B has an effective coil area of the effective coil area of coil 842C. If coil 842D is in electrical communication with a load, and coil 842C is not in electrical communication with a load, the implantable inductive communication component 842B has an effective coil area of the effective coil area of coil 842D, and coil 842D functions as an inductance coil. Thus, through the use of switches 1070A and 1070B, implantable inductive communication component 842B is configured to vary the effective coil area of the component.

An embodiment of the present invention includes an external device that includes an external inductive communication component that is configured to vary the effective coil area of the component, and an implantable component that includes an implantable inductive communication component that configured to vary the effective coil area of the component. Accordingly, such an embodiment may correspond to a cochlear implant that includes the external device 704 of FIG. 7 and the implantable component 844B of FIG. 8B.

An embodiment of the present invention includes an inductive communication component configured to vary the effective coil area of the component that includes more than two coils. In an exemplary embodiment, the loops of three or more coils are arrayed concentrically about one another. In an exemplary embodiment, referring to external inductive communication component 716, a third coil (or fourth, etc.) is added in between coil 716A and coil 716B of external inductive communication component 716 of FIG. 7. This third (or forth, etc.) coil is electrically isolated from the other coils as well. In an embodiment, additional coils are added to the implantable inductive communication component 842B in a similar manner.

It is noted that in an exemplary embodiment of the present invention, when the coil is decoupled from the power supply or the load (i.e., disconnected), such as may be accomplished through the use of the switches described herein (which may be MEMS switches), the parasitic loss associated with the decoupled or unused coil is negligible (as compared to about a 10-50 μF loss if the coil is not decoupled from the power supply or load).

As noted above, FIG. 9 depicts another exemplary embodiment of an inductive communication component 916 configured to vary the effective coil area of the component. The inductive communication component 916 includes a coil that may be physically adjusted to vary the effective coil area of the inductive communication component 916. In this regard, inductive communication component 916 includes a looped wire 916A. In an embodiment, the looped wire 916A is spring loaded (by, for example, the wire itself or a separate component) such that the looped wire 916A has a memory which imparts an outward (expansive) force onto the looped wire 916A. That is, the looped wire 916A would expand outward, thus increasing the diameter D, if the ends of the looped wire 916A were not under tension. Accordingly, by increasing the tension on the ends of the looped wire 916A, the effective coil area of the coil formed by the looped wire 916A may be reduced. Conversely, by decreasing the tension on the ends of the looped wire 916A, the effective coil area of the coil formed by the looped wire 916A may be enlarged.

In an exemplary embodiment, looped wire 916A partially winds about pinions 919 to capstans 920A and 920B. The looped wire is at least partially wound about capstans 920A and 920B. Capstans 920A and 920B may be actuated manually or by an electric motor (not shown) or other type of motor to rotate clockwise and/or counterclockwise to variously reel in and reel out looped wire 916A. For example, if capstan 920A is rotated clockwise and capstan 920B is rotated counterclockwise, looped wire 916A is reeled in because looped wire 916A becomes more wound about the capstans. When the looped wire 916A is reeled in, the mean diameter D of the coil formed by the looped wire 916A is reduced, and thus the effective coil area of the coil 916A is reduced. Conversely, if capstan 920A is rotated counterclockwise and capstan 920B is rotated clockwise, looped wire 916A is reeled out because looped wire 916A becomes unreeled from the capstans. When the looped wire 916A is reeled out, the mean diameter D of the coil formed by the looped wire 916A is enlarged (because of, for example, the spring force on the looped wire 916A mentioned above), and thus the effective coil area of inductive communication component 916 is enlarged. It is noted that in an embodiment, only one capstan may be present, the other end of the looped wire 916A being fixed to a non-rotating element. It is further noted that in an embodiment, the pinions 919 may move horizontally or vertically or diagonally to change the effective coil area of the inductive communication component 916.

In yet another embodiment, the effective coil area of a coil may be varied by varying the orientation or degree of overlap with the other coil of an inductance communication component system. In an exemplary embodiment, the location of a magnet or other ferrous material of one or both of the inductive communication components may be adjustable such that coils of an exterior inductive communication component are not concentric with the coils of an implantable inductive communication component. This has the effect of changing the coupling factor k of the implantable inductive communication component system.

In an embodiment of the present invention, an inductive communication component configured to vary the effective coil area of the component comprises two coils arrayed side-by side, as opposed to one coil encompassing the other coil in a substantially coaxial fashion. In such an embodiments, the coils have different effective coil areas, and the effective coil area of the inductive communication component configured to vary the effective coil area of the component is varied by moving the opposite coil of the inductive communication component system to be opposite one or the other of the side-by-side coils. In such an embodiment, each of the side-by-side coils includes a magnet or other ferrous material located substantially concentrically inside each coil, such that the magnet or other ferrous material of the opposite coil of the inductance communication component system will center on a given coil as desired. In yet another embodiment, there is an inductive communication component configured to vary the effective coil area of the component system that include a plurality of removably attachable coils (to/from, for example, the cable 703 of the external device 704 of FIG. 7, or the body of the implantable component 844A/844B) each having different effective coil areas. Depending on the performance characteristics of the prosthesis, one of the plurality of coils is selected and attached to the prosthesis, thereby varying the effective coil area of the coils of the prosthesis.

An embodiment of the present invention includes methods, systems and apparatuses configured to implement those methods and systems, to vary the effective coil area of an inductive communication component. An embodiment of the present invention further includes methods, systems and apparatuses configured to implement those methods and systems, to identify how (e.g., by what amount) the effective coil area of an inductive coil component should be varied. More specifically, an embodiment of the present invention includes a method of choosing, including automatically choosing, between coils of an inductive communication component to obtain desired performance characteristics of a prosthesis. Further, an embodiment includes identifying how, including automatically identifying how, a physically adjustable coil of an inductive communication component configured to vary the effective coil area of the component should be adjusted to obtain desired performance characteristics of a prosthesis.

The performance characteristics of the prosthesis may include the voltage of the implant measured at, for example, the implantable coil. Below are presented methods and algorithms that may be used, in some exemplary embodiments, to accomplish this end. Some of these methods and algorithms rely on telemetry from the implantable component. Accordingly, before describing such methods and algorithms, an exemplary telemetry link usable with some embodiments of the present invention will now be described, where the exemplary telemetry link is focused on communicating a measured implant voltage $U_{L2}$ to an external device, where the external device evaluates that communicated measured implant voltage to make determinations as to a desired effective coil area of an inductive communication component.

Figure 13:
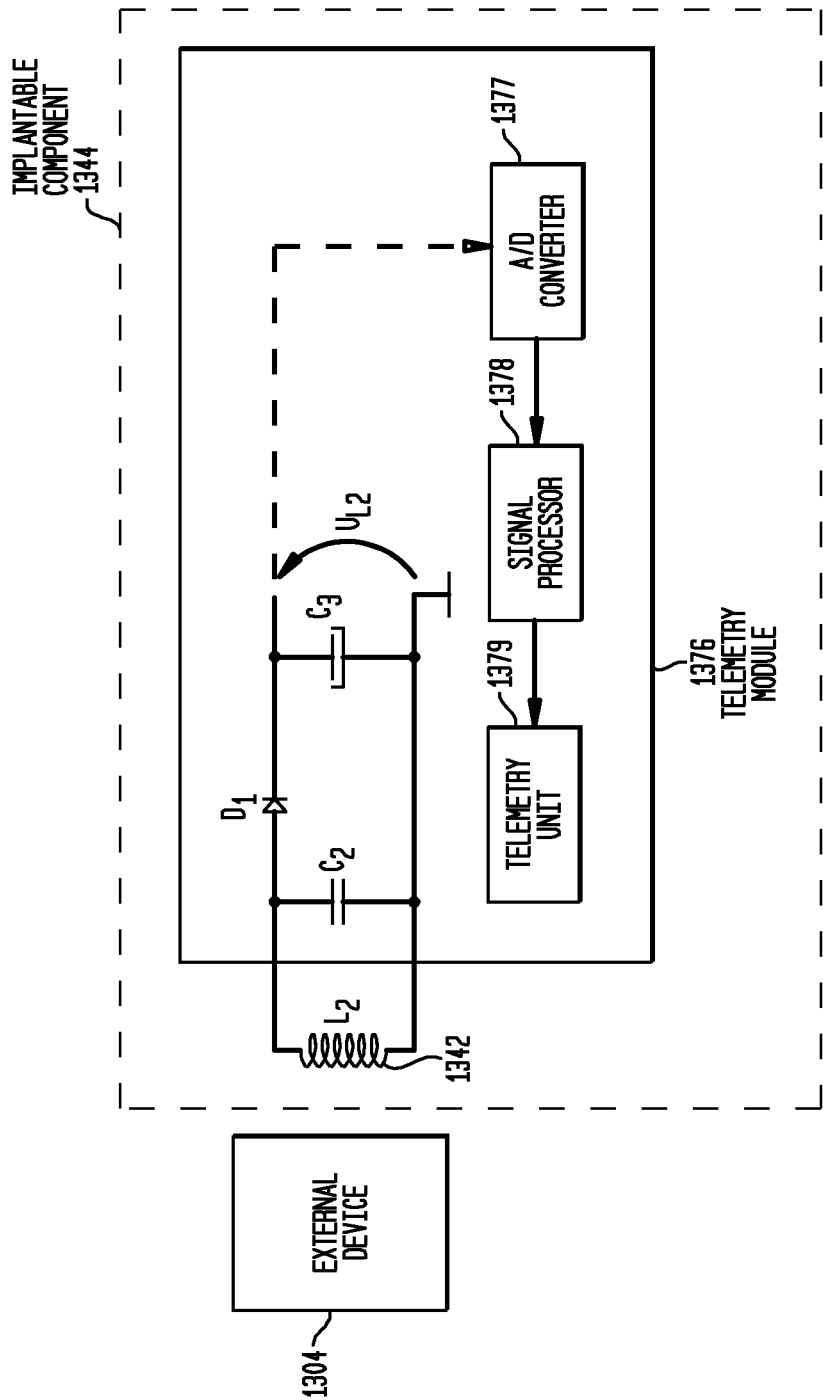
FIG. 13 is a simplified circuit diagram of a telemetry module in accordance with embodiments of the present invention.

FIG. 13 illustrates an external device 1304 and an exemplary implantable component 1344 which may include, respectively, some or all of the features of the various external devices and implantable components described above. Implantable component 1344 includes a coil 1342, which may be a standard coil as detailed above, or may be an inductive communication component configured to vary the effective coil area of the component, either of which may receive power via magnetic induction from external device 1304. The embodiment depicted in FIG. 13 includes a telemetry link that may be implemented for communicating performance characteristics and other information pertaining to a prosthesis, such as a measured implant voltage $U_{L2}$, to the external device. As illustrated, implantable component 1344 comprises a telemetry module 1376, that may be used to establish a telemetry link. The telemetry link is a wireless transcutaneous communication link between the implantable component 1344 and the external device 1304 that is ultimately established by telemetry unit 1379, and may be via an electromagnetic coupling, capacitive coupling, magnetic coupling, optical coupling, auditory coupling or ultrasonic coupling. By communicating performance characteristics (e.g., implant voltage) to the external device 1304, the performance characteristics of the implantable component 1344 may be monitored, and the effective coil area of the inductive communication component may be varied accordingly.

In the embodiment depicted in FIG. 13, the implant voltage, $U_{L2}$, is converted from an analogue signal to a digital signal by A/D converter 1377. Signal processor 1378 processes the digital signal received from A/D converter into a signal indicative of the implant voltage $U_{L2}$, and this signal indicative of the implant voltage $U_{L2}$, is sent to telemetry unit 1379. The signal indicative of the implant voltage $U_{L2}$ is communicated to the external device 1304 via telemetry unit 1379. Telemetry unit 1379 may use coil 1342 or may use a separate coil. In an exemplary embodiment, the telemetry module 1376 may be used to monitor the efficiency of the power link. Based on the monitored efficiency, the effective coil area of the inductive communication components described herein may be varied.

Based on the performance characteristic(s) that are monitored and communicated to the external device 1304, the external device 1304 may automatically control the selection of the coils and/or control how a coil should be physically adjusted. For example, for embodiments wherein two or more coils and coil switching circuitry are provided in the external device (e.g., the embodiment of FIG. 10), a processor in the external device may select one coil over another coil for use as the induction coil. Still further by example, for embodiments wherein a coil is physically adjustable (e.g., the embodiment of FIG. 9), a processor in the external device may determine how the effective coil area of the coil should be adjusted. Alternatively, coil selection/coil adjustment selection may be performed by the implantable device and selection instructions are provided to the external device via the telemetry link. In another embodiment, the implant voltage $U_{L2}$ or other performance characteristic may be communicated to another device external to the recipient. Such a device may be a device used for fitting an implant, such as a cochlear implant. That is, in an exemplary embodiment, the effective coil area of an inductive communication component may be varied shortly after the implantable component is implanted. This may be done, for example, in instances where there is no concern for varying implant load, at least initially, and the driving concern relates more to the impact of skin flap thickness, etc.

Figure 14:
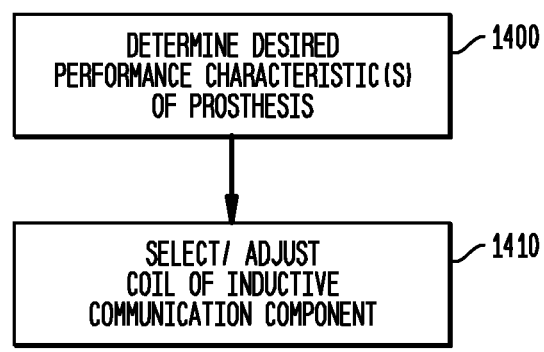
FIG. 14 is a flow-chart of an exemplary method in accordance with embodiments of the present invention.

FIG. 14 presents an exemplary flow chart corresponding to a method of varying an effective coil area of an inductive communication component. The method may be implemented via a processor included in the external device or the implantable component of the prostheses described herein, or may be included in any other convenient location. Accordingly, the method may be automatically executed.

At step 1400 in FIG. 14, the desired performance characteristic(s) of a prosthesis are determined. In an exemplary embodiment, the performance characteristic is a voltage of the implantable component measured at the implantable coil, as detailed above with respect to telemetry module 1376. At step 1410, the desired coil from amongst a plurality of coils of an inductive communication component is selected (e.g., coil 716A or coil 716B in FIG. 7) and/or the coil of an inductive communication component is physically adjusted (e.g., coil 916A in FIG. 9) to obtain the desired performance characteristics and/or to move the actual performance characteristics more closer to the desired performance characteristics.

Figure 15:
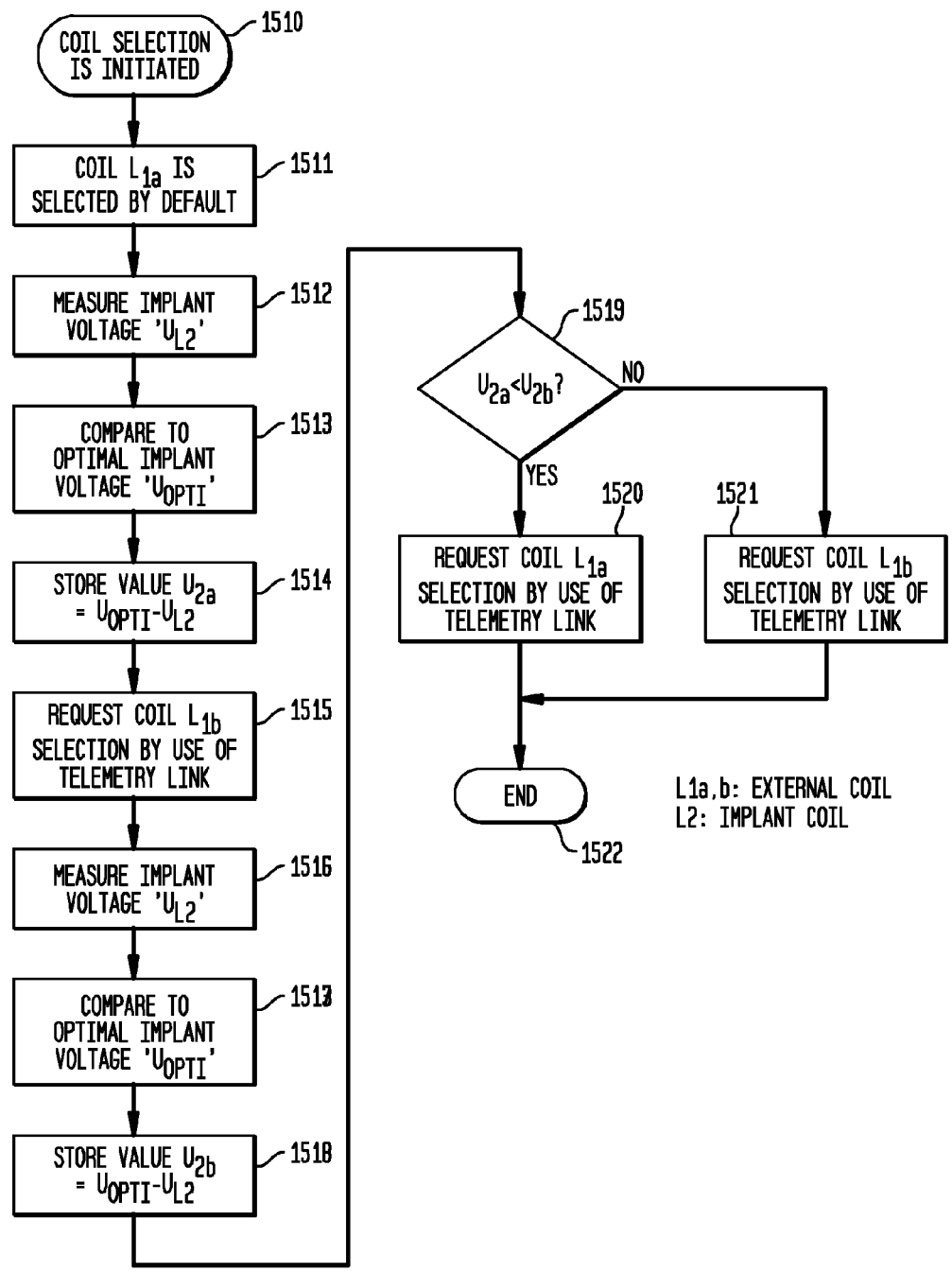
FIG. 15 is another flow-chart of an exemplary method in accordance with embodiments of the present invention.

FIG. 15 provides additional details of an exemplary embodiment of implementing step 1410, where a desired performance characteristic has already been identified ($U_{opti}$). Specifically, an embodiment of the present invention includes an algorithm that may be used to determine, including automatically determine, which coil(s) should be utilized in an inductive communication component having multiple coils, such as that depicted in FIG. 7.

FIG. 15 provides an exemplary algorithm for coil selection to improve power transmission. FIG. 15 will discussed with reference to the above discussed FIGS. 7 and 8A. That is, the algorithm of FIG. 15 is presented in terms of an inductive communication component with two coils $L_{1a}$ and $L_{1b}$ located on the external device, and a standard coil with a single coil L2 located on the implantable component. As will be understood, the algorithm may be modified to take into account the use of implantable coils 842B of FIG. 8B.

At step 1510 of FIG. 15, the coil selection process is initiated. At step 1511, coil $L_{1a}$ is selected (i.e., coil $L_{1a}$ is placed into electrical communication with a supply of power) by default when the initial magnetic induction connection is established. At step 1512, the efficiency of this initial power link is determined by measuring the implant voltage $U_{L2}$, which is the effective voltage across the implantable coil. At step 1513, the measured implant voltage $U_{L2}$ is compared with a predetermined optimal implant voltage $U_{opti}$ and at step 1514 the difference is calculated and stored as $U_{2a}$. Next, at step 1515, coil $L_{1b}$ is selected as the inductance coil using a switching circuit to place coil $L_{1b}$ into electrical communication with a power supply, thus establishing a second power link. At step 1516, the implant voltage $U_{L2}$ of the second power link is measured and at step 1517 compared with $U_{opti}$. At step 1518, the difference is calculated and stored as $U_{2b}$. At step 1519, $U_{2a}$ and $U_{2b}$ are then compared to determine which power link provides an implant voltage closer to the optimal implant voltage. If $U_{2a}$ is less than $U_{2b}$, at step 1520, coil $L_{1a}$ is identified for use in the external inductive communication component. If $U_{2a}$ is not less than $U_{2b}$, at step 1521, coil $L_{1b}$ is selected for use in the external inductive communication component. At step 1522, the algorithm ends.

It is again noted that information regarding $U_{L2}$, etc., may be transmitted to the external device via a telemetry link utilizing the telemetry circuit depicted in FIG. 13.

Figure 9:
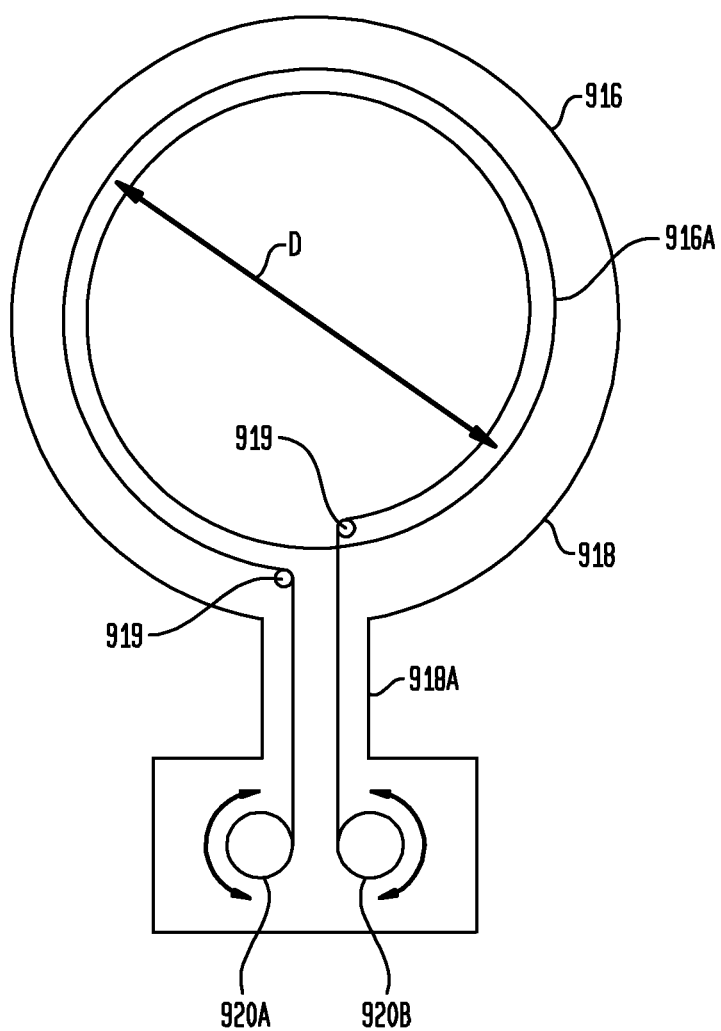
FIG. 9 is a simplified schematic diagram of a communication component configured to vary the effective coil area in accordance with embodiments of the present invention.

It is further noted that in the algorithm depicted in FIG. 15, instead of selecting different coils, the effective coil area of a coil, such as that corresponding to coil 916 of FIG. 9, that may be physically adjusted, and empirical data pertaining to the voltage of the implantable component may be obtained. Using the empirical data, the better effective coil area of the coil may be identified. In an exemplary embodiment, the effective coil areas of the physically adjustable coil are binary. That is, the physically adjustable coil, such as coil 916, may be adjusted for only two effective coil areas. However, in other embodiments, the physically adjustable coil may be adjusted such that it can have more than only two effective coil areas (it may have three, four or more effective coil areas, etc.). In this regard, the physically adjustable coil may be a continuously variable effective coil area inductive communication component, where the effective coil area may be varied over a great number of effective coil areas.

While the comparisons in the algorithm of FIG. 15 between $U_{2a}$ and $U_{2b}$ are made via logic residing in an external device, in other embodiments, an implantable component may include a processor that implements logic for comparing $U_{2a}$ and $U_{2b}$, identifying the appropriate coil/coil adjustment, and communicating this identification across the telemetry link. In some embodiments, such as where the inductive communication component configured to vary the effective coil area of the component is an implantable coil, no information pertaining to the identification of the appropriate coil is transmitted, as the effective coil area of the coil is varied by the implantable component because the inductive communication component configured to vary the effective coil area of the component is implantable.

It is noted that while the algorithm of FIG. 15 relies on the implant voltage as measured at the implantable coil, other embodiments, may utilize other parameters, such as current, etc. It is further noted that while the above embodiment utilized real-time measurements of the voltage of the system, other embodiments may be implemented where the effective coil area of the coil is adjusted based on how measurable features impact the performance characteristics of the prosthesis. By way of example, during implantation of the implantable component, the skin flap thickness may be measured, and, based on this measurement, the effective coil area of the inductive communication component may be varied (either manually or automatically). Still further, measurements may be taken exterior to a recipient regarding physical phenomenon that are indicative of performance characteristics of a prosthesis, such as, for example, the amount of reflective inductance associated with the implantable coil. Based on these measurements, the effective coil area of the coil is varied.

Still further, in an exemplary embodiment, the actual effective coil area of the coil(s) that provides the desired performance characteristics may be determined, and the effective coil area of one or more coils may be varied accordingly. This is in contrast to the algorithm of FIG. 15, where only the voltages associated with two different coils was determined, and the coil that provided the better voltage was selected. In an exemplary embodiment, the actual effective coil areas of the coils that provides the desired performance characteristics may be determined empirically (such as by varying effective coil area and/or the distance D between the coils in discrete increments) and/or analytically (such as by using the simplified and/or rigorous equations detailed above). Based on the determination of the actual effective coil area that is desired, the effective coil areas of the inductive communication component may be varied so that the effective coil areas are closer to and/or substantially the same as the desired actual effective coil area. Such a regime may have utility in embodiments where, for example, an inductive communication component configured to vary the effective coil area of the component includes a coil that is physically adjustable in a substantially continuous matter, as the coil may be physically adjusted to achieve substantially the exact desired effective coil area.

An embodiment of the present invention includes a dynamic system whereby the effective coil area of the inductive communication component configured to vary the effective coil area of the component is adjusted to address changing performance characteristics. For example, as noted above, the load on an implantable coil will vary in the event that an implantable battery fails, where, in such a scenario, the power to drive a an implantable stimulating device must instantaneously be transmitted by an inductance communication component system. Accordingly, the algorithm of FIG. 15 could be executed periodically during the implantation life of an implantable component so that such a change in performance characteristics can be address. In yet another embodiment, there is an algorithm that includes varying the effective coil area of an inductive communication component to improve power transmission to an implantable component, with a goal of improving power transmission towards optimum power transmission (power transmission optimization.) Still further, as noted above, an implantable component may have different performance characteristics depending on whether or not the implantable component is recharging a rechargeable battery. In an exemplary embodiment, the effective coil area of the inductive communication component may be varied based on the current mode of the prosthesis, as opposed to, or in addition to, measured performance characteristics.

Figure 16:
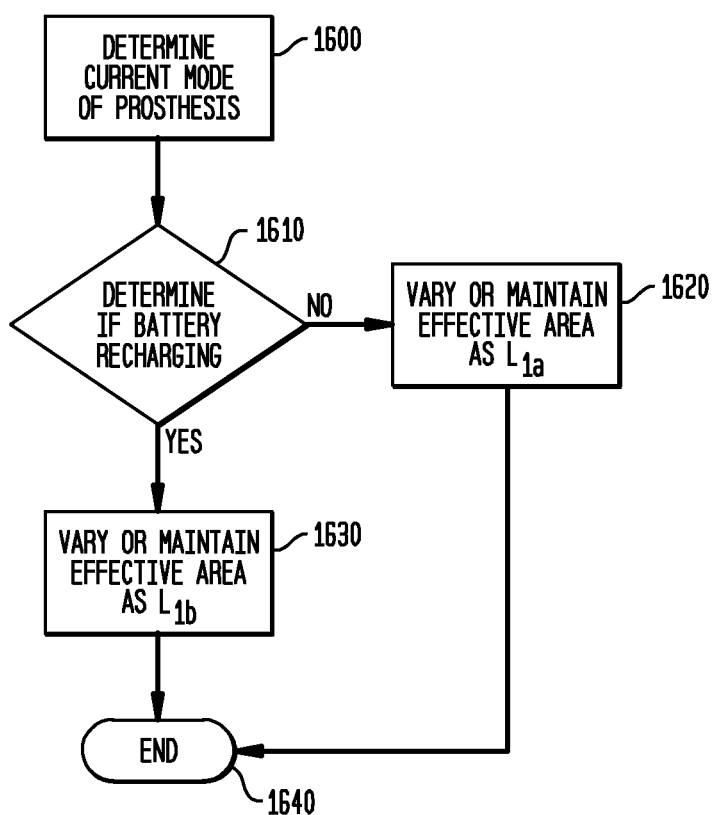
FIG. 16 is yet another flow-chart of an exemplary method in accordance with embodiments of the present invention.

According to an embodiment of the present invention, the effective coil area of an inductive communication component may be varied depending on the mode of a prosthesis. For example, FIG. 16 provides an exemplary algorithm that is based on a determination as to whether or not a prosthesis is in a battery recharging mode. The exemplary algorithm of FIG. 16 may be included in logic in a processor located in the external device or the implantable component of the prostheses described herein, or in any other convenient component. A method paralleling the algorithm presented with regard to FIG. 16 may be performed automatically using a processor or the like.

In FIG. 16, at step 1600, a processor in the prosthesis determines the current mode of the prosthesis. At step 1610, a determination is made by a processor if the current mode is a mode entailing the recharging of an implantable battery rechargeable battery. If a determination is made that the mode is not a mode entailing the recharging of an implantable battery, the algorithm proceeds to step 1620, where the effective coil area is varied or maintained in view of the determination that the prosthesis is not in a mode entailing the recharging of an implantable battery. If a determination is made that the mode is a mode entailing the recharging of an implantable battery, the algorithm proceeds from step 1610 to step 1630, where the effective coil area is varied or maintained in view of the determination that the prosthesis is in a mode entailing the recharging of an implantable battery. After both steps 1620 and 1630, the algorithm proceeds to step 1640, where the algorithm ends.

It will be appreciated that in some embodiments of the present invention, additional determinations may be included. In some embodiments, a determination may be made as to whether the prosthesis is in a monopolar electrode stimulation mode, a bipolar electrode stimulation mode, or any other mode where performance characteristics may be improved by varying the effective coil area. In this regard, the algorithm of FIG. 16 may be varied accordingly. Alternatively, step 1640 of FIG. 16 may not be the end of the algorithm, but instead, a processor may continue to a new determination step, such as a determination step that entails whether or not the prosthesis is in a monopolar electrode stimulation mode, etc., in which case the effective coil area may be varied (or not varied).

It is noted that embodiments of the present invention may be practiced with any type of prosthesis where power and/or data is transferred transcutaneously via magnetic induction. Exemplary embodiments have been described above with respect to a cochlear implant. Other embodiments in which power and/or data may be transferred according to the present invention include, but are not limited to, other types of hearing prostheses including middle ear implants, bone conduction devices, traditional hearing aids, hybrid systems which combine, for example, a cochlear implant with a traditional hearing aid. Further, embodiments may be utilized with FES, etc.

At least some embodiments of the present invention, when properly implemented, may provide an improved power link for a given operating condition, and/or dynamically adjust the link via varying the effective coil area in response to varying operating conditions. Further, at least some embodiments of the present invention, when properly implemented, may provide improved power transfer efficiency, reduction in the waste of power, and/or reduces heating of the external device and/or the implantable component as a result of, for example, power loss. Further, at least some embodiments of the present invention, when properly implemented, may reduce prosthesis start-up time and/or charging times and/or reduce a risk of device failure and/or degraded performance due to power link failure and/or inefficiencies. These as compared to a similarly situated prosthesis that does not utilize an inductive communication component configured to vary the effective coil area of the component according to the present invention (e.g., an identical prosthesis except for the absence of such an inductive communication component).

Another exemplary embodiment of the present invention includes varying the effective coil area of the inductive communication component(s) and detuning the resonant circuits of the external device and the implantable component so that, in combination, the two actions change the performance characteristics of the implantable component (e.g., the voltage measured at the implantable inductive communication component).

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of transcutaneously transmitting power from an external device to an implantable component of a prosthesis implanted in a recipient, comprising:
    transmitting power during a first temporal period from the external device through skin of the recipient to the implantable component via an inductive communication component system including an inductance coil;
    varying, after the first temporal period, a coupling factor k of the inductive communication component system; and
    transmitting, after the first temporal period and after varying the coupling factor k, power from the external device through skin of the recipient to the implantable component of the prosthesis via the inductive communication component system,
    wherein the coupling factor k is varied by varying a ratio of an effective coil area of an external inductive communication component to an effective coil area of an implanted inductive communication component ($A_1/A_2$) of the system, and
    the method further comprises increasing a voltage of the implantable component by reducing a value of $A_1/A_2$.

2. The method of claim 1, further comprising removing a first inductance coil exterior to the recipient from the inductance communication component system and replacing the first inductance coil with a second inductance coil having an effective coil area different than that of the first inductance coil, thereby also varying the coupling factor k of the system.

3. The method of claim 1, further comprising measuring a voltage of the implantable component before varying $A_1/A_2$, and automatically varying $A_1/A_2$ based on the measured voltage of the implantable component.

4. The method of claim 1, wherein:
    the action of changing, after the first temporal period, the coupling factor k of the inductive communication component system entails energizing a first portion of the communication component not energized during the first temporal period.

5. The method of claim 1, wherein:
    the action of varying, after the first temporal period, the coupling factor k of the inductive communication component system entails varying the coupling factor k while an orientation of an external coil of the inductive communication component system remains same relative to a skin of a recipient as the orientation of the external coil during the first temporal period.

6. The method of claim 1, wherein:
    the action of varying, after the first temporal period, the coupling factor k of the inductive communication component system is an automatic action.

7. The method of claim 1, wherein the actions of transmitting power during the first temporal period, varying the coupling factor k, and transmitting, after the first temporal period, power from the external device are executed using an external coil that is in series resonance with a first capacitor and an implanted coil that is in parallel resonance with second capacitor, at or close to a magnetic inductance operating frequency of the inductive communication component system, the second capacitor also being in series with the implanted coil.

8. A method of transcutaneously transmitting power from an external device to an implantable component of a prosthesis implanted in a recipient, comprising:
    transmitting power during a first temporal period from the external device through skin of the recipient to the implantable component via an inductive communication component system including an inductance coil;
    varying, after the first temporal period, a coupling factor k of the inductive communication component system; and
    transmitting, after the first temporal period and after varying the coupling factor k, power from the external device through skin of the recipient to the implantable component of the prosthesis via the inductive communication component system, wherein $A_1/A_2$ is varied from a value of 1 to a value of 0.4 or less.

9. A method of transcutaneously transmitting power from an external device to an implantable component of a prosthesis implanted in a recipient, comprising:
    transcutaneously transmitting power during a first temporal period from the external device through skin of the recipient to the implantable component via an inductive communication component system with an inductance coil having a first effective coil area, wherein the external device and the implantable component comprise a system having a coupling factor k during the first temporal period; and
    transcutaneously transmitting, after the first temporal period, power from the external device through skin of the recipient to the implantable component of the prosthesis via the inductive communication component system with the same inductance coil but having a second effective coil area different from that of the first effective coil area,
    wherein the action of transmitting the power during the first temporal period entails energizing a first inductance coil portion of the inductance coil including at least a first looped wire, wherein the action of transmitting the power after the first temporal period entails energizing a second inductance coil portion of the inductance coil including at least a second looped wire that was not energized during the first temporal period, thus resulting in an effective coil area of the inductance coil having the second effective coil area, and wherein the first inductance coil has a first effective coil area and the second inductance coil has a second effective coil area that is less than the first effective coil area.

10. The method of claim 9, wherein a ratio of the first effective coil area to the second effective coil area is 2 to 1.

11. The method of claim 9, further comprising, after the first temporal period, vary a coupling factor between the first inductive communication component and the second inductive communication component.

12. The method of claim 9, wherein the external device is an external device of a cochlear implant, wherein the internal device is a receiver/stimulator of the cochlear implant.

13. The method of claim 9, further comprising the action of transcutaneous communicating stimulation data to the implantable component using the inductance coil having the first effective coil area.

* * * * *